(12) United States Patent
Nelsestuen

(10) Patent No.: US 6,423,826 B1
(45) Date of Patent: Jul. 23, 2002

(54) HIGH MOLECULAR WEIGHT DERIVATIVES OF VITAMIN K-DEPENDENT POLYPEPTIDES

(75) Inventor: Gary L. Nelsestuen, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/607,716

(22) Filed: Jun. 30, 2000

(51) Int. Cl.$^7$ .............................................. C07K 14/745
(52) U.S. Cl. ...................... 530/345; 530/384; 530/308; 424/94.63; 435/180; 435/181; 520/8; 520/54.1
(58) Field of Search ................ 424/94.63; 435/180, 435/181; 530/345, 300, 384; 520/8, 54.1

(56) References Cited

U.S. PATENT DOCUMENTS

| 5,217,705 A |   | 6/1993  | Reno et al. |
| 5,580,560 A |   | 12/1996 | Nicolaisen et al. |
| 5,788,965 A |   | 8/1998  | Berkner et al. |
| 5,817,788 A |   | 10/1998 | Berkner et al. |
| 5,824,639 A |   | 10/1998 | Berkner |
| 5,833,982 A |   | 11/1998 | Berkner et al. |
| 5,861,374 A |   | 1/1999  | Berkner et al. |
| 5,990,079 A | * | 11/1999 | Wolf et al. |
| 6,017,882 A |   | 1/2000  | Nelsestuen |
| 6,037,452 A |   | 3/2000  | Minamino et al. |
| 6,110,721 A | * | 8/2000  | Gibbs et al. |

FOREIGN PATENT DOCUMENTS

| JP | 8 092294    | 4/1996  |
| WO | WO 91/09125 | 6/1991  |
| WO | WO 94/29370 | 12/1994 |
| WO | WO 97/11957 | 4/1997  |
| WO | WO 98/32466 | 7/1998  |
| WO | WO 99/20767 | 4/1999  |
| WO | WO 01/02439 | 1/2001  |
| WO | WO 01/58935 | 8/2001  |

OTHER PUBLICATIONS

Banner et al., *Nature*, 1996 380:41–46.
Beauchamp et al., *Anal. Biochem.*, 1983, 131(1):25–33.
Furie et al., *Cell*, 1988, 53:505–518.
Harker et al., *Thromb. Haemost.*, 1997, 78:736–741.
Hedner et al., *Transfus. Med. Rev.*, 1993, 7(2):78–83.
Lee et al., *Bioconjugate. Chem.*, 1999, 10:973–981.
Luo et al., *Nature*, 1997, 386:78–81.
Manfioletti et al., *Mol. Cell. Biol.*, 1993, 13(8):4976–4985.
McDonald et al., *Biochemistry*, 1997, 36:5120–5127.
Monroe et al., *Brit. J. Haemat.*, 1997, 99:542–547.
Muir et al., *Curr. Opin. Biotechnol.*, 1993, 4:420–427.
Nelsestuen, *Trends. Cardiovasc. Med.*, 1999, 9(6):162–167.
Nelsestuen et al., *Vitam. Horm.*, 2000, 58:355–389.
Shah et al., *Proc. Natl. Acad. Sci. USA*, 1998, 95:4229–4234.
*Shearwater Polymers, Inc.*, 2000, Catalog, p. 11.
*Shearwater Polymers, Inc.*, 2000, Catalog, p. 20.
*Shearwater Polymers, Inc.*, 2000, Catalog, p. 34.
*Shearwater Polymers, Inc.*, 2000, Catalog, p. 41.
Shen et al., *J. Biol. Chem.*, 1998, 273(47);31086–31091.
Sorenson et al., *J. Biol. Chem.*, 1997, 272(18):11863–11868.
Spanier et al., *J. Thorac. Cardiovasc. Surg.*, 1998, 115(5):1179–1188.

* cited by examiner

*Primary Examiner*—Jon P. Weber
(74) *Attorney, Agent, or Firm*—Fish & Richardson, P.C., P.A.

(57) ABSTRACT

Modifications of vitamin K-dependent polypeptides that lead to enhanced protein function on a weight or molar basis and/or increase of protein lifetime in the circulation are described. Both objectives are important for using vitamin K-dependent polypeptides for pro- and anti-coagulation therapies, as well as for other uses in the circulation.

16 Claims, 11 Drawing Sheets

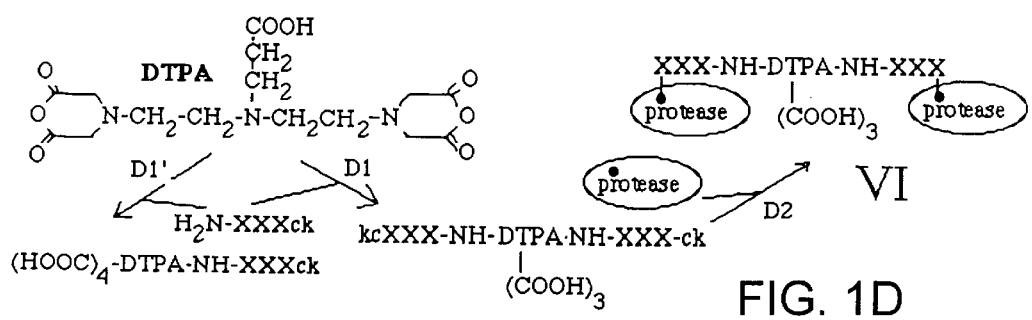
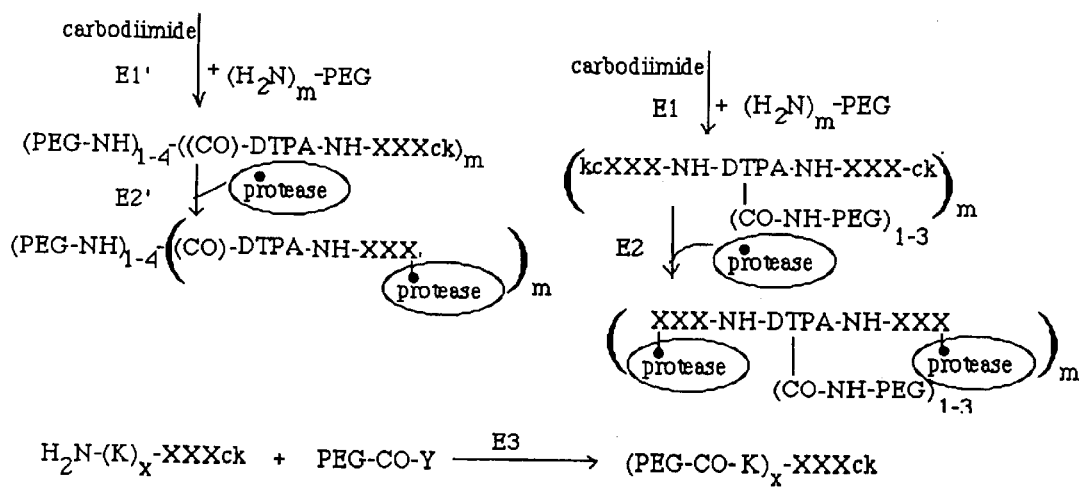
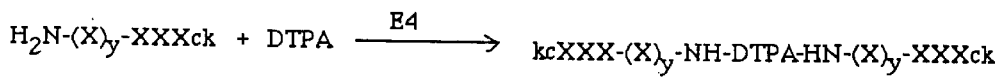
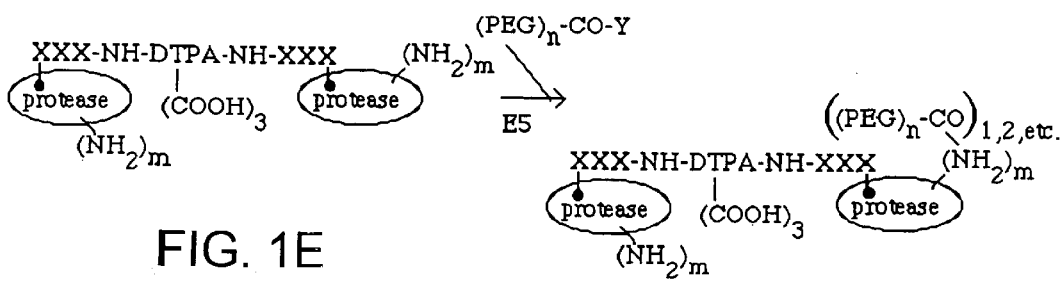
FIG. 1D
FIG. 1E

HIGH MOLECULAR WEIGHT DERIVATIVES OF VITAMIN K-DEPENDENT POLYPEPTIDES

STATEMENT AS TO FEDERALLY-SPONSORED RESEARCH

Funding for work described herein was provided in part by the federal government, which may have certain rights in the invention.

TECHNICAL FIELD

This invention relates to high molecular weight derivatives of vitamin K-dependent polypeptides, and more particularly to dimerized vitamin K-dependent polypeptides and vitamin K-dependent polypeptides that are linked to PEG polymers.

BACKGROUND

Vitamin K-dependent proteins contain 9 to 13 gamma-carboxyglutamic acid residues (Gla) in their amino terminal 45 residues. The Gla residues are produced by enzymes in the liver that utilize vitamin K to carboxylate the side chains of glutamic acid residues in protein precursors. Vitamin K-dependent proteins are involved in a number of biological processes, of which the most well described is blood coagulation (reviewed in Nelsestuen (2000) *Vitam. Horm.* 58:355–389). Vitamin K-dependent proteins include protein Z, protein S, prothrombin (factor II), factor X, factor IX, protein C, factor VII, Gas6, and matrix GLA protein. Factors VII, IX, X and II function in procoagulation processes while protein C, protein S and protein Z serve in anticoagulation roles. Gas6 is a growth arrest hormone encoded by growth arrest-specific gene 6 (gas6) and is related to protein S. See, Manfioletti et al. (1993) *Mol. Cell. Biol.* 13:4976–4985. Matrix GLA protein normally is found in bone and is critical to prevention of calcification of soft tissues in the circulation. Luo et al. (1997) *Nature* 386:78–81.

The regulation of blood coagulation is a process that presents a number of leading health problems, including both the failure to form blood clots as well as thrombosis, the formation of unwanted blood clots. Agents that prevent unwanted clots are used in many situations and a variety of agents are available. Unfortunately, most current therapies have undesirable side effects. Orally administered anticoagulants such as Warfarin act by inhibiting the action of vitamin K in the liver, thereby preventing complete carboxylation of glutamic acid residues in the vitamin K-dependent proteins, resulting in a lowered concentration of active proteins in the circulatory system and reduced ability to form clots. Warfarin therapy is complicated by the competitive nature of the drug with its target. Fluctuations of dietary vitamin K can result in an over-dose or under-dose of Warfarin. Fluctuations in coagulation activity are an undesirable outcome of this therapy.

Injected substances such as heparin, including low molecular weight heparin, also are commonly used anticoagulants. Again, these compounds are subject to overdose and must be carefully monitored.

A newer category of anticoagulants includes active-site modified vitamin K-dependent clotting factors such as factor VIIa and IXa. The active sites are blocked by serine protease inhibitors such as chloromethylketone derivatives of amino acids or short peptides. The active site-modified proteins retain the ability to form complexes with their respective cofactors, but are inactive, thereby producing no enzyme activity and preventing complexing of the cofactor with the respective active enzymes. Thus, active-site modified Factor VIIa, denoted factor VIIai, still binds tissue factor, but does not have enzyme activity. Active site-modified proteins appear to have very beneficial anti-coagulant properties with few undesirable side affects. For example, factor VIIai has been shown to lower platelet deposition at the site of surgery, an important indicator of anti-coagulation action. While this can also be accomplished by heparin or other anticoagulants, factor VIIai was unique in that its administration was not accompanied by increased bleeding time or blood loss. See, Harker et al. (1997) *Thromb. Haemost.* 78:736–741. A similar outcome was reported when factor IXai was administered during surgery. See, Spanier et al. (1998) *J. Thorac. Cardiovasc. Surg.* 115(5):1179–88. In short, these proteins appear to offer the benefits of anticoagulation therapy without the adverse side effects of other anticoagulants. Active site modified factor Xa is another possible anticoagulant in this group. Its cofactor protein is factor Va. Active site modified activated protein C (APC) may also form an effective inhibitor of coagulation. See, Sorensen et al. (1997) *J. Biol. Chem.* 272:11863–11868. Active site modified APC binds to factor Va and prevents factor Xa from binding.

A major inhibition to the use of active site-modified vitamin K-dependent clotting factors is cost. Biosynthesis of vitamin K-dependent proteins is dependent on an intact glutamic acid carboxylation system, which is present in a small number of animal cell types. Overproduction of these proteins is severely limited by this enzyme system. Furthermore, the effective dose of these proteins is high. A common dosage is 1000 $\mu$g of VIIIai/kg body weight. See, Harker et al. 1997 supra. Current cost (April of 2000) of recombinant factor VIIa is about $0.80 per $\mu$g, which severely limits use.

A second problem for several of these proteins is a short lifetime in the circulation system. The situation for factor VIIa illustrates this problem. Factor VII and VIIa have circulation half-times of about 2–4 hours in the human. That is, within 2–4 hours, half of the protein is taken up by other tissues of the body. When factor VIIa is used as a procoagulant to treat certain forms of hemophilia, the standard protocol is to inject VIIa every two hours and at high dosages (45 to 90 $\mu$g/kg body weight). See, Hedner et al. (1993) *Transfus. Med. Rev.* 7:78–83. Thus, use of these proteins as procoagulants or anticoagulants (in the case of factor VIIai) requires that the proteins be administered at frequent intervals and at high dosages.

SUMMARY

The invention is based, in part, on modifications to vitamin K-dependent polypeptides that increase their circulation half-life and in some embodiments, their activity. Both outcomes reduce the amount of protein needed to treat clotting disorders as well as decrease the frequency of administration. As a result, costs associated with treating patients can be reduced, allowing the therapies to be made more widely available to individuals in need of pro- or anti-coagulation therapies.

In one aspect, the invention features an isolated vitamin K-dependent polypeptide linked (e.g., directly or indirectly) to a polyethylene glycol (PEG) polymer. The polypeptide can be selected from the group consisting of factor VII, factor IX, factor X, factor II, protein C, protein S, gas6, and bone matrix Gla protein or can be a protease selected from the group consisting of factor VIIa, factor IXa, factor Xa, factor IIa, and activated protein C. Factors VIIa, IXa, and Xa are particularly useful proteases. The protease can be further linked to an active-site inhibition reagent such as a chloromethylketone derivatized amino acid or peptide. In some embodiments, the PEG polymer is linked to the protease via the active-site inhibition reagent.

The invention also features an active-site inhibition reagent linked to a PEG polymer. The reagent can be a chloromethylketone derivatized amino acid or peptide or a phosphohalide derivative.

In another aspect, the invention features an anticoagulant agent that includes two polypeptide monomers, wherein at least one of the polypeptide monomers is a vitamin K-dependent polypeptide, and wherein the polypeptide monomers are covalently linked. The polypeptide monomers can be covalently linked via a bi-functional active-site inhibition reagent. The two polypeptide monomers can be the same or different polypeptides. In some embodiments, each of the two polypeptide monomers is a vitamin K-dependent polypeptide, such as a factor VIIa polypeptide, a factor Xa polypeptide, or a factor IXa polypeptide. The bi-functional active-site inhibition reagent can be linked to a PEG polymer. At least one of the polypeptide monomers also can be directly linked to a PEG polymer.

The invention also features a bi-functional active-site inhibition reagent that includes two covalently linked active-site inhibitors. At least one of the active-site inhibitors can be linked to a PEG polymer.

A method of directly linking a vitamin K-dependent polypeptide to a PEG polymer also is featured. The method includes incubating the PEG polymer with the vitamin K-dependent polypeptide for a time sufficient to link the PEG polymer to the vitamin K-dependent polypeptide, wherein the PEG polymer is reactive with amino groups or carbohydrate groups on the vitamin K-dependent polypeptide.

In yet another aspect, the invention features a method of indirectly linking a vitamin K-dependent polypeptide to a PEG polymer. The method includes providing a PEG-modified, active-site inhibition reagent, wherein the PEG polymer is reactive with amino groups on the active-site inhibition reagent; and incubating the PEG-modified, active-site inhibition reagent with the vitamin K-dependent polypeptide for a time sufficient to link the PEG modified, active-site inhibition reagent to the vitamin K-dependent polypeptide.

A method of making an anticoagulant agent also is featured. The method includes incubating a bi-functional active-site inhibition reagent and at least one vitamin K-dependent polypeptide in the presence of phospholipid for a time sufficient to link the bi-functional active-site inhibition reagent and the vitamin K-dependent polypeptide.

In another aspect, the invention features a pharmaceutical composition that includes an isolated vitamin K-dependent polypeptide linked to a PEG polymer and a pharmaceutically acceptable carrier. The polypeptide and PEG polymer can be indirectly linked. The polypeptide can be a protease selected from the group consisting of factor VIIa, factor IXa, factor Xa, factor IIa, and activated protein C. Factors VIIa, IXa, and Xa are particularly useful proteases. The protease can be further linked to an active-site inhibition reagent such as a chloromethylketone derivatized amino acid or peptide. The PEG polymer can be linked to the protease via the active-site inhibition reagent.

The invention also features a pharmaceutical composition that includes an anticoagulant agent and a pharmaceutically acceptable carrier, wherein the anticoagulant agent includes two polypeptide monomers, wherein at least one of the polypeptide monomers is a vitamin K-dependent polypeptide, and wherein the polypeptide monomers are covalently linked. The polypeptide monomers can be covalently linked via a bi-functional active-site inhibition reagent.

In yet another aspect, the invention features a method for evaluating dosage of factor VIIa. The method includes obtaining a biological sample from a patient undergoing factor VIIa therapy; and monitoring clotting time of the biological sample in a device, wherein the device comprises an activator of the contact phase of coagulation and is lacking added phospholipid, wherein a sufficient decrease in clotting time compared to a control sample from the patient before the factor VIIa therapy indicates that an appropriate dosage of factor VIIa has been administered. Factor VIIa therapy can include administering to the patient factor VIIa linked to a PEG polymer.

The invention also features a method for managing anticoagulation therapy in a patient. The method includes administering an acute phase anticoagulant to the patient during the acute phase of coagulation; and administering an active-site inhibited factor VIIa polypeptide to the patient during the chronic phase of coagulation. The active-site inhibited factor VIIa polypeptide can be linked to a PEG polymer, as described above. The acute phase anticoagulant can be active-site modified factor IXa or active-site modified Xa.

Pharmaceutical compositions that include an active-site inhibited factor VIIa polypeptide and an acute phase anticoagulant also are featured. The active-site inhibited factor VIIa polypeptide can be linked to a PEG polymer, as described above. The PEG polymer can be linked to the active-site inhibited factor VIIa polypeptide via an active-site inhibition reagent.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIGS. 1A–1E are schematics of strategies for modifying vitamin K-dependent polypeptides.

FIG. 2A is a graph of clotting time versus concentration of VIIai (solid circles) and dimeric VIIai (open circles when calculated on the basis of monomer concentration and open squares when calculated on the basis of dimer concentration). FIG. 2B is a Hill type plot of the data shown in FIG. 2A.

FIG. 4A is a comparison of wild type factor VIIai (solid circles) with monomeric VIIai(P10Q/K32E) (open triangles), dimeric VIIai(P10Q/K32E) containing over 50% dimer (open circles), and VIIai(P10Q/K32E) containing traces of dimer (open squares). FIG. 4B is a comparison of wild type VIIai (solid circles) with mutant VIIai(P10Q/K32E) (open squares) and a heterodimer of mutant VIIai(P10Q/K32E)-Xa (open triangles).

In FIG. 6A, factor VIIa and calcium were added to anticoagulated blood of two hemophilia patients (open circles and solid circles), just before assaying. Titration with the factor VIIa mutant, P10Q/K32E (solid squares), is shown for the same patient who received wild-type VIIa (shown in solid circles). FIG. 6B provides results for blood from a normal individual that had been treated with anti-VIII antibody to create severe VIII deficiency. Experiments are shown for wild type VIIa (open circles), the VIIa-P10Q/K32E mutant (open squares), PEG-derivatized wild type VIIa (solid diamonds), and PEG-derivatized VIIa-P10Q/K32E (solid circles).

In FIG. 7A, titrations for VIIai (solid circles), VIIai-PEG-3.4k (open squares), VIIai-PEG-20k (solid triangles), and VIIai-PEG-40k (open triangles) are presented. In FIG. 7B, the circulation half-life (in hr) is shown for the samples of FIG. 7A, plotted as a function of the molecular weight of the PEG attached to the protein.

FIG. 8A shows results for three animals that were administered VIIai (solid circles, open diamonds, and inverted triangles), one animal that was administered dimeric VIIai (open squares), and two animals that were administered VIIai-PEG-3.4k (solid triangles and solid diamonds). FIG. 8B provides the turnover of randomly modified VIIai. Two lines are drawn for the first three and the last three data points. VIIai is shown for reference (solid circles).

FIG. 9A depicts factor VIIai inhibition in acute coagulation (open circles) and chronic coagulation (solid circles) and Q10E32ai inhibition of acute coagulation (open squares) and chronic coagulation (solid squares). FIG. 9B is a time course for inhibition by factor VIIa, the conversion from acute to chronic anticoagulation. Results are for 10 nM factor VIIai-WT (open squares), 0.4 nM Q10E32ai (open circles), 3.8 nM Q10E32ai (solid squares), 4 nM factor VIIa-WT (open triangles), and 0.17 nM Q10E32ai (solid circles).

DETAILED DESCRIPTION

Figure 1A:
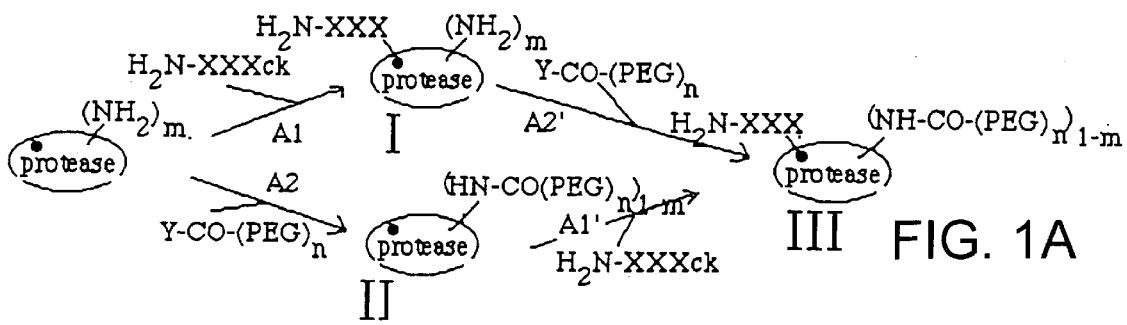

Vitamin K-dependent polypeptides are a group of proteins that utilize vitamin K in their biosynthetic pathways to carboxylate the side chains of glutamic acid residues in protein precursors. The GLA domain contains 9–13 γ-carboxyglutamic acid residues in the N-terminal region of the polypeptide, typically from amino acid 1 to about amino acid 45. Protein Z, protein S, factor X, factor II (prothrombin), factor IX, protein C, factor VII, Gas6, and bone matrix GLA protein are examples of vitamin K-dependent polypeptides that are useful in the invention. Furthermore, useful vitamin K-dependent polypeptides can be wild-type or can contain mutations. Particularly useful factor VII and protein C mutations are described in Shah et al. (1998) *Proc. Natl. Acad. Sci. USA* 95:4229–4234 and Shen et al. (1998) *J. Biol. Chem.* 273:31086–3101, respectively, in which enhancements in protein function were reported. Also see U.S. Pat. No. 6,017,882 for additional mutations. Many clotting factors, including factors VII, IX, X, and prothrombin, are zymogens, i.e., inactive proenzymes, and are converted during coagulation to active serine proteases.

FIG. 1 provides a general description for making the derivatives of vitamin K-dependent polypeptides of the invention. The polypeptides presented in FIG. 1 are described as proteases. It should be noted, however, that many of the reactions, including reactions A2, A2' and E5, can be used with any vitamin K-dependent polypeptide.

Vitamin K-dependent Polypeptides Linked to PEG Polymers

The invention features isolated vitamin K-dependent polypeptides linked to polyethylene glycol (PEG) polymers. An "isolated polypeptide" has been separated from cellular components that naturally accompany it. Typically, the polypeptide is isolated when it is at least 60% (e.g., 70%, 80%, 90%, or 95%), by weight, free from proteins and naturally-occurring organic molecules that are naturally associated with it. As used herein, the term "polypeptide" is any chain of at least five amino acids that retains the ability to bind cofactors or membranes. Amino acids have been designated herein by standard three letter and one-letter abbreviations.

Derivatization of amino groups on the surface of proteins (m in FIG. 1A) with PEG-containing compounds can extend the circulation time of some proteins and reduce their potential antigenic properties. See, Beauchamp et al. (1983) *Anal. Biochem.* 131(1):25–33. In general, the greatest impact on circulation time has been with longer chain PEG polymers, with a molecular weight up to about 15,000. PEG modified proteins typically are low molecular weight proteins that are cleared from the circulation by pinocytosis in the kidney, such as a Fv fragment of an antibody molecule, and proteins that act on low molecular weight substrates, such as superoxide dismutase, asparaginase, and hemoglobin. Lee et al. (1999) *Bioconjugate. Chem.* 10:973–981; and Shearwater Polymers, Inc. (2000) Catalog, p. 41, Huntsville, Ala. The increase of molecular weight by addition of PEG to low molecular weight proteins is thought to enhance circulation lifetime by eliminating a specific clearance process.

PEG-derivatization of proteins also can reduce protein antigenicity. Thus, PEG derivatization can reduce or prevent antibody production to a foreign protein. Without being bound by a particular mechanism, a 'polymer cloud' of PEG may diffuse at the surface of the protein, obliterating the surface for the macromolecular recognition system of antibody production. Shearwater Polymers, Inc. (2000) Catalog, p 11. Based on this mechanism, PEG modification may hinder interaction of the modified protein with other macromolecules while allowing small molecule diffusion near the protein surface such that substrate access to the active site is virtually unchanged. Thus, activity of proteins with low molecular weight substrates, such as superoxide dismutase, is not altered, whereas binding between an antibody and antigen may be diminished with multiple PEG derivatizations. See, Lee et al. (1999) *Bioconjugate. Chem.* 10:973–981.

Based on this, factor VII and other vitamin K-dependent polypeptides such as factors IX, X, and II that interact with cofactor proteins, membrane surfaces, or both, appear to be unlikely targets for PEG modification. For example, factor VIIa must interact with tissue factor, a macromolecular cell surface receptor that includes a large area of the factor VIIa surface, and with a membrane surface. See, Banner et al. (1996) *Nature* 380:41–46. The presence of a polymer cloud over the factor VIIa surface would be expected to interfere with both of these critical interactions. In addition, the vitamin K-dependent polypeptides occur naturally in the plasma and have molecular weights that are high enough to avoid rapid removal through the kidney. As described herein, however, vitamin K-dependent polypeptides that are linked to PEG have an increased lifetime in the circulation, with little or no impact on activity.

The term "linked" is used herein to include 1) both direct, covalent links and indirect links (i.e., through an intermediate molecule) of a PEG polymer to a polypeptide; 2) covalent coupling of a PEG polymer to an intermediate molecule such as an active-site inhibition reagent; 3) covalent coupling of an active-site inhibition reagent to a protease; and 4) direct, covalent links and indirect links (i.e., through an intermediate molecule) of polypeptide monomers to each other. In some embodiments, the PEG polymer is directly and indirectly linked to the vitamin K-dependent polypeptide. Suitable PEG polymers can vary in length and valency with respect to the number of PEG chains per reactive site, n or m in FIG. 1. Typically, PEG polymers contain an activated ester (—CO—Y) and can react with protein amino groups to form a covalent linkage. Many standard leaving groups (Y) are known and are available commercially. Non-limiting examples of leaving groups include p-nitrophenol and succinimidyl propionate (SPA). In addition to activated esters, other standard approaches exist for crosslinking a reagent to amino groups on the protein surface, including, for example, aldehyde-containing PEG molecules. The aldehyde forms a Schiff's base with is amino groups on the protein. The Schiff's base is selectively reduced with sodium cyanoborohydride in a well-described reaction. This chemistry is available commercially. See, Shearwater Polymers, Inc. (2000) Catalog, p. 20. Another process for attaching groups such as PEG to glycoproteins uses periodate to oxidize carbohydrates to aldehydes, followed by addition of hydrazide derivatives of the group to be attached. The hydrazide reacts with the aldehydes to produce a stable link. Hydrazide derivatives of PEG polymers are available commercially, for example, from Shearwater Polymers, Inc. and appropriate reaction conditions are described in the Shearwater Polymers, Inc. catalog (2000, p. 34). Many of the vitamin K-dependent polypeptides are glycoproteins and therefore subject to this chemistry.

PEG polymers can be directly linked to vitamin K-dependent polypeptides, including active-site modified proteases, by randomly reacting the PEG polymer with protein amino moieties. Reactions in FIG. 1A produce heterogeneous products (1 to m derivatives at random locations) as a typical polypeptide may have 20 amino groups on its surface and there is little basis for chemical selectivity. As described herein, a population of factor VIIai molecules with randomly linked PEG had circulation lifetimes that were 20 times greater than those of the wild type protein, although activity was slightly less. While products II and III in FIG. 1 are heterogeneous with respect to both the number of PEG attachments and location of the PEG on the polypeptides, these preparations have potential value to therapy. Standardization of reaction conditions can create preparations with consistent properties that may be beneficial for both pro- and anticoagulation therapy.

Figure 1B:
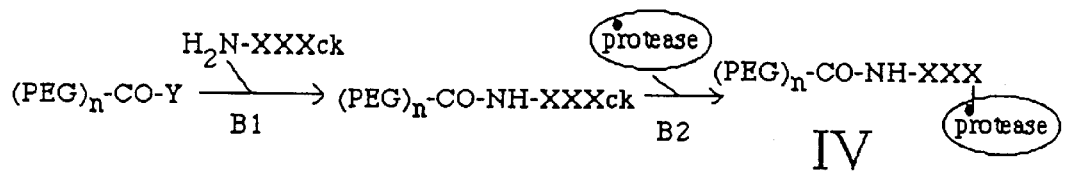
Figure 1C:
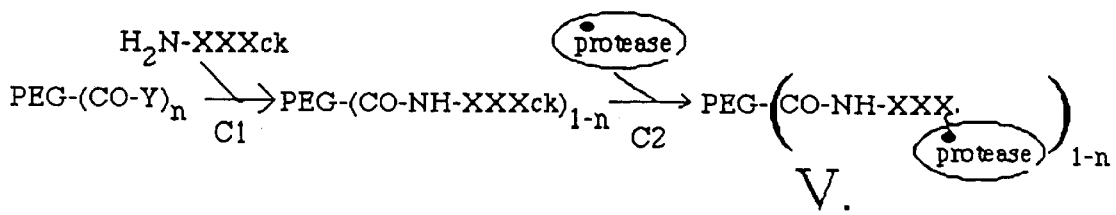

Reactions B1 and B2 of FIG. 1B illustrate methods used to indirectly derivatize polypeptides by attachment of the PEG polymer through the active site of the protease. In general, a PEG polymer and an active-site inhibition reagent (described below) can be covalently linked to form a PEG-modified active-site inhibition reagent before reacting with an activated vitamin K-dependent polypeptide, such as factor VIIa, IXa, Xa, or IIa. Since the active-site-directed inhibitor has a single amino group, only one product (compound IV) is generated from reaction B1. Unreacted active-site-directed reagent can be removed by dialysis or gel filtration chromatography. The PEG polymer has a high molecular weight and these simple procedures allow quantitative separation from unreacted reagent. The active ester on the PEG moiety (—CO—Y) is slowly hydrolyzed by water, and incubation for a period of time can remove excess reactive reagent. Thus, it may not be necessary to remove any excess PEG before proceeding with step B2. Once all of the activated ester is destroyed by water hydrolysis, step B2 can be initiated.

In step B2, the PEG-modified, active site-directed reagent reacts with the protease, with negligible side reactions, to produce a single entity. Excess PEG, in any form, can be removed by ion exchange chromatography on a material such as DEAE-Sephadex, which is a standard step in the purification of vitamin K-dependent polypeptides. These polypeptides bind tightly to anion exchange material at low salt (e. g. 0.1 M NaCl, pH 7.0) and are eluted by high salt (e. g. 0.5 M NaCl). As unreacted PEG polymers have little charge (the active site-directed reagent is cationic, if it is present) and do not bind to an anion exchange resin, the polymers can be removed by washing the column with low salt buffer before eluting with high salt. The reactions described in FIG. 1B can use a range of leaving groups (Y) or other strategies for derivatizing amino groups as outlined above. Purification of the final product may not be necessary as unreacted PEG polymers are biologically inert and active-site inhibition reagents may not pose adverse effects.

Circulation lifetime was determined by the size of the PEG polymer attached. One preparation had a circulation half-time that was almost 20-fold greater than that of normal VIIai. The magnitude of impact of PEG on circulation time of factor VIIai was very surprising, given that this protein is a naturally occurring plasma protein and that it is not subject to removal as a low molecular weight peptide. The PEG derivatives of blood clotting proteases described herein provide an enormous advantage for use in either procoagulant (e.g. factor VIIa or IXa) or anticoagulant (Factor VIIai, IXai, Xai or IIai) therapy. The longer circulation time not only decreases the amounts needed for anticoagulation over time, but also greatly diminishes the frequency with which the anticoagulants have to be administered by injection.

In some embodiments, PEG polymers having more than one reactive group (e.g., 2–4) per polymer can be used to modify the vitamin K-dependent polypeptide. PEG polymers with more than one reactive group are commercially available from, for example, Shearwater Polymers, Inc. PEG polymers with other combinations of reactive groups can be generated by chemical synthesis using known chemistry. The reactions in FIG. 1C utilize multivalency of reactive groups on the PEG polymer to generate multivalency with respect to active-site modified proteases. Quantitative yields in reaction C1 are difficult to achieve due to water hydrolysis of the active ester. In addition, with, e.g., four reactive groups per polymer, one can expect PEG products containing 0, 1, 2, 3, and 4 active site-directed inhibitors. Purification of each product is possible, although more complex than purification of compound IV in FIG. 1B. Since the active-site-directed inhibitor typically contains the side chain of an arginine residue, each active-site inhibition reagent that is present adds a charge and the products can be separated by ion exchange chromatography. Each peptide of the active-site inhibition reagent also can enhance affinity of the product for reverse phase chromatography on a C18 column.

Active Site Inhibition Reagents

Chloromethylketones or organic phosphohalides such as diisopropylfluorophosphate (DIFP) can be used to modify the active-site of proteases that are vitamin K-dependent polypeptides. Chloromethylketones can be single amino acids such as tosylysylchloromethylketone (TLCK) or short peptides and are commercially available. Phenylalanylprolylarginylchloromethylketone (FPRck, also known as PPACK) is available from Calbiochem, San Diego, Calif. and is described by the manufacturer as a good inhibitor of thrombin and factor VIIa, among other enzymes. Phenylalanylphenylalanylarginylchloromethylketone (FFRck, also known as PPACK II) is available from Calbiochem and is another example of a commonly available peptide. Glutamylglycylarginylchloromethylketone (EGRck) can be used with a derivative at its amino termimus, such as the fluorescent derivative, Dansyl-EGRck (DEGRck), and also is available from Calbiochem.

Reactions A1 and A1' of FIG. 1 depict reaction of a chloromethylketone derivative (ck) of an active site-directed peptide or amino acid ($H_2N$-XXX) with the active site of a blood clotting protease (e.g., Factor VIIa, IXa, Xa, thrombin or factor IIa) to create an inactive enzyme (VIIai, Xai, IXai, IIai).

Oligomers of Vitamin K-dependent Polypeptides

The invention also features anticoagulant agents that include oligomers of vitamin K-dependent polypeptides. In general, the anticoagulant agent includes at least two polypeptide monomers that are covalently cross-linked. At least one of the polypeptide monomers is a vitamin K-dependent polypeptide, while the second polypeptide monomer can be the same or a different vitamin K-dependent polypeptide, a protease, (e.g., trypsin), or a polypeptide that contains a membrane-binding site. Annexin polypeptides are non-limiting examples of polypeptides that contain a membrane binding site. FIG. 1D provides reactions for producing a homodimer of active site-modified blood clotting proteases. Heterodimers can be produced in a similar manner. Homodimer refers to a dimer containing two identical polypeptides, while heterodimer refers to a dimer containing two different polypeptides. Typically, a bifunctional reagent is reacted with an active-site inhibition reagent (reaction D1 and D1'), and the resulting bifunctional active-site inhibition reagent, containing two active-site inhibitors, is isolated. The monovalent product also can be isolated and may be useful in some embodiments. Diethylenetriaminepentacetic acid anhydride (DTPA) is an example of bifunctional reagent that can be used. Many other bifunctional reagents that react with amines are available commercially. For example, the Pierce Chemical Co. (Rockford, Ill.) has 49 bifunctional reagents available that react with amines.

HPLC chromatography can be used to separate univalent products from divalent products. The bifunctional active-site inhibition reagent can be used to create various homodimers and heterodimers of blood clotting proteases, such as compound VI of FIG. 1D. Addition of phospholipid vesicles to the reaction can increase dimer yield. In some cases, heterodimers may be more effective in vivo due to simultaneous inhibition of several steps of coagulation. For example, a factor Xai-factor IXai dimer can inhibit factors VIIIa and Va at the same time, while a VIIai-Xai dimer can inhibit tissue factor and factor Va at the same time. Homo- and heterodimers can be purified by standard methods, including, for example, gel filtration chromatography.

As described herein, dimers of wild type factor VIIai enhanced protein-cofactor-membrane binding by about 16-fold, which is much less than the theoretical increase of $10^6$ to $10^{11}$-fold. The heterodimer of VIIa and factor Xa produced a 25-fold increase in competitive binding to tissue factor-membrane, much less than the theoretical level of about $10^7$-fold. Factor Xa has a Kd for membrane association of about $10^{-7}$. See, McDonald et al. (1997) *Biochemistry* 36:5120–5127. Dimerization of a mutant of factor VIIa (P10Q/K32E), which has higher affinity for the membrane than wild type factor VIIa, did not result in detectable improvement of binding affinity. See, Shah et al., supra, for a description of the mutant. This indicates that minor changes in the membrane-binding site altered the ability to participate in simultaneous binding. The heterodimer of mutant VIIa and factor Xa actually had reduced affinity for tissue factor-membrane than did monomeric mutant VIIai. While a 16–35-fold improvement in affinity can have a large impact on therapeutic value of a drug, this range is a very small part of the total free energy of the multiple binding events.

Dimerized, Active-site Modified, PEG-linked Vitamin K-dependent Polypeptides

As described above, PEG polymers can be introduced to random surface amine groups or to the active site of a protease to enhance its circulation time and active site-modified enzymes can be dimerized to enhance function. Such protein modification strategies can be combined to provide dimeric, active site-modified proteases that are linked to PEG polymers, resulting in polypeptides with up to several hundred-fold enhancement of function over wild type, monomeric, active site-modified proteases. Well-known and established chemistries can be used to produce such modified polypeptides, as illustrated in FIG. 1E. Reactions E1, E2, E1' and E2' are continuations of the DTPA dimerization shown in FIG. 1D and combine dimer formation and introduction of PEG into the same molecule. Both DTPA derivatives of the active site-directed inhibitor contain carboxyl groups but no amino groups. The DPTA derivatives can be crosslinked to appropriate amines by well-known reactions such as that of carbodiimide, a reagent that is commonly used for amide and peptide bond synthesis. Both the monomeric and dimeric inhibitor products can be modified by these reactions.

When univalent PEG is used as the source of amino groups (m=1 in FIG. 1E), a range of products can be produced that differ in the number of PEG polymers attached to the active-site-directed reagent. For example, a divalent active site-directed intermediate can produce a modified polypeptide that has the longer circulation time provided by PEG and the higher activity of dimeric VIIai. An intermediate with a single active-site-directed inhibition reagent can produce an inhibitor with the advantage of multiple PEG polymers, giving enhanced circulation lifetime.

If multivalent PEG (m>1, FIG. 1E) is used as the source of amino groups, complex products can be produced such as an oligomer of monomers (reaction E2') or an oligomer of dimers (reaction E2). Products generated by reactions E1 and E2 may be heterogeneous due to difficulty in obtaining quantitative or strictly controlled reaction with carbodiimide. Nevertheless, heterogeneity does not prevent formation of useful products. Since mulivalency occurs on both the amino group and the carboxyl group, some products may be extremely large.

Reaction E3 outlines a strategy for introducing multiple PEG polymers to the active site of a vitamin K-dependent protease. This can be accomplished, for example, by using an active-site inhibition reagent that includes additional amino groups. The example shown in reaction E3 is a short polylysine chain ($K_y$). The PEG-linked product can be coupled to factor VIIa by reaction B2.

Crosslinkers with longer spacer arms can be produced by reaction E4, using the reactions described in FIG. 1D, but with different active-site inhibition reagents. Use of linker arms of different length is well-established in crosslinking technology. Several crosslinking agents with different lengths (e.g. linker arms of 2 to >1000 atoms) are available from commercial sources such as the Pierce Chemical Co. and the Sigma Chemical Co. For example, elongated, bifunctional active-site inhibition reagents with more than three amino acids can be produced and the remaining reactions carried out as in FIG. 1B. The advantage of reaction E4 may be the ability to utilize a wider range of proteins. Using a longer linker arm, generated by the simple modification shown in reaction E4 (or numerous other strategies), may result in dimers with enhanced activity.

Reaction E5 shows another benefit of dimeric proteins. That is, random derivatization of a dimer with one PEG polymer leaves one polypeptide monomer without modification. That is, addition of one PEG polymer to a dimeric polypeptide leaves one polypeptide monomer completely underivatized and free to bind to its receptor or cofactor protein. In fact, by random attachment, fifty percent of a dimer population that has an average of two PEG polymers attached still will have one polypeptide monomer that is underivatized. The use of dimeric proteins may allow very high order PEG substitution with retention of substantial activity, as randomly derivatized monomeric factor VIIai retained function to the level of at least one PEG per molecule.

Assay for Factor VIIa Therapy

The invention also provides an assay for factor VIIa therapy that can detect individual variation in sensitivity to VIIa and help target dosage levels for individual patients. No assay is presently available to detect therapeutic response to factor VIIa administration in an individual hemophilia patient. Assays for hemophilia A and B, its severity and the level of correction by infusion of VIII or IX clotting factors are normally conducted with a plasma clotting assay known as the APTT time. This assay depends on activation of the intrinsic blood clotting cascade (factor XII) by agents such as Kaolin or Ellagic acid. Upon addition of calcium, XIIa activates XI, which activates IX, and coagulation occurs. This assay therefore depends on factors IX and VIII levels in the plasma and is sensitive to both hemophilia A and B. A problem for factor VIIa therapy is that its mechanism of action may differ from the normal cascade. That is, factor VIIa can bind to phospholipid surfaces and activate factor X directly, without use of tissue factor, factor IX, or factor VIII. See, Monroe et al. (1997) *Brit. J. Haemat.* 99:542–547. In the absence of tissue factor, factor VIIa is a relatively poor enzyme. In addition, factor VIIa has relatively low affinity for a membrane.

Assays that depend on externally added phospholipid do not represent the true procoagulant status of patients undergoing factor VIIa therapy, as phospholipid content influences the outcome of the assay. For example, at high phospholipid concentration, wild type factor VIIa and a mutant factor Via protein (P10Q/K32E) have nearly identical activities, while at low phospholipid concentration, an 8-fold difference is observed between the wild type and mutant protein.

As described herein, clotting time can be more accurately monitored by using an assay containing biological membranes rather than phospholipids. Since individuals will vary with respect to their cellular activity, the assay should use the cells of the patient undergoing therapy, at the time at which therapy is administered. Thus, the invention features a method for evaluating dosage of factor VIIa, including PEG-modified factor VIIa. Biological samples such as whole blood are obtained from a patient before and after factor VIIa administration and clotting time is monitored. Typically, a device such as the HEMOCHRON® Jr. from International Technidyne or a similar instrument is used to facilitate the measurement. Such devices contain optical detectors that monitor coagulation time by detecting the speed at which the blood moves between two of the optical detectors. Other devices use resistance to mechanical agitation such as stirring or flow under pressure to detect clotting time. The activated clotting time (ACT) assay and specific instrumentation such as the HEMOCHRON® Jr. microcoagulation apparatus typically are devoted to monitoring anticoagulation therapy during surgery or other procedures. The results herein, however, indicate that the ACT can provide the necessary conditions required to monitor procoagulation response in hemophilia patients receiving factor VIIa.

The biological sample from the patient undergoing factor VIIa therapy is placed in a cuvette or similar container that includes an activator of the contact phase of coagulation and that is lacking added phospholipid. Non-limiting examples of activators of the coagulation phase include Celite, kaolin and ellagic acid. The biological sample and the cuvette contain all necessary components for the reaction. Thus, the cuvette containing the biological sample is placed in the device and clotting time is measured. The clotting times of samples before and after factor VIIa therapy are compared to determine if clotting time has significantly decreased. If a sufficient decrease in clotting time is observed after factor VIIa administration, a sufficient dosage of factor VIIa has been administered. A sufficient decrease in clotting time refers to the restoration of hemostasis in the patient. If clotting time has not sufficiently improved, factor VIIa dosage can be modified appropriately.

Alternatively, titration curves, similar to those shown in FIG. 6, may be constructed before administration of VIIa to an individual. Individual response to factor VIIa is relatively constant over time. Therefore, prospective candidates for factor VIIa therapy can have a titration curve performed ahead of time and used to design therapy when needed.

Acute and Chronic Phases of Coagulation

The invention also provides a method for managing anticoagulant therapy in a patient. The method includes administering an acute phase anticoagulant to a patient during acute coagulation and administering a factor VIIai polypeptide to the patient during chronic coagulation. "Chronic" anticoagulation refers to equilibrium conditions and can occur when factor VIIa and VIIai are incubated with tissue factor for a time sufficient to reach equilibrium before coagulation is initiated. The assays of FIGS. 2–4 are examples of assays performed under chronic anticoagulation conditions. In contrast, "acute" anticoagulation refers to all components related to coagulation and anticoagulation being initiated simultaneously. The assay described in FIG. 5, which required Xai to inhibit coagulation, exemplifies acute coagulation. That is, the receptor for Xai, factor Va, is not present until coagulation begins.

Most anticoagulants target materials that are not present until coagulation has begun and therefore act in an 'acute' manner. For example, heparin stimulates antithrombin III inhibition of thrombin; thrombin is not present until coagulation has been initiated. A large number of active site inhibitors of clotting enzymes such as thrombin, Xa, IXa and VIIa all act on a coagulation process that has been initiated. The receptors for factors IXai and Xai (factors VIIIa and Va, respectively) are not present until coagulation has begun. Thus, factor VIIai may provide a unique form of anticoagulation that is referred to herein as 'chronic' anticoagulation.

A chronic anticoagulation state can be reached when tissue factor is exposed to the circulation for a prolonged period of time, initiating continual, but very limited, coagulation events. This condition may exist for some time before the tissue factor is removed from the circulation, allowing factor VIIai to reach binding equilibrium and creating 'chronic' anticoagulation. Acute coagulation occurs when the endothelium is damaged, e.g., during angioplasty. After this initial phase, however, chronic coagulation conditions may exist when tissue factor is present for a prolonged period of time. Administration of factor VIIai, and especially factor VIIai with high affinity for tissue factor-membrane, such as dimeric VIIai and mutants with high membrane affinity, during this chronic phase is an effective method of anticoagulation treatment. Although VIIai can prevent acute coagulation, higher dosages are needed. Thus, for many situations such as catheterization, angioplasty, and surgery, effective anticoagulation therapy may be to use a combination of anticoagulants, a highly effective inhibitor of acute coagulation during the procedure that generates tissue injury (such as endothelial cell damage during angioplasty) and factor VIIai to prevent the chronic coagulation that follows. Treatment with VIIai might require several days to provide continual protection until healing is complete and tissue factor is entirely removed from the circulation. Using PEG-derivatized and/or dimerized proteins (e.g., VIIai, Xai, IXai) as acute anticoagulants or chronic anticoagulants during anticoagulation therapy can reduce dosages and reduce the frequency of administration.

Production of Modified Vitamin K-dependent Polypeptides

Isolated vitamin K-dependent polypeptides are commercially available from, for example, Novo Nordisk (Princeton, N.J.). Vitamin K-dependent polypeptides can be produced in transgenic animals or by cell culture. Preferably, the transgenic animal or eukaryotic host can carboxylate the glutamic acid residues of the vitamin K-dependent polypeptide. To produce vitamin K-dependent polypeptides by cell culture, a nucleic acid encoding the polypeptide is ligated into a nucleic acid construct such as an expression vector, and eukaryotic host cells are transformed with the expression vector. In general, nucleic acid constructs include a regulatory sequence operably linked to a nucleic acid sequence encoding a vitamin K-dependent polypeptide. Regulatory sequences do not typically encode a gene product, but instead affect the expression of the nucleic acid sequence. As used herein, "operably linked" refers to connection of the regulatory sequences to the nucleic acid sequence in such a way as to permit expression of the nucleic acid sequence. Regulatory elements can include, for example, promoter sequences, enhancer sequences, response elements, or inducible elements.

In eukaryotic host cells, a number of viral-based expression systems can be utilized to express vitamin K-dependent polypeptides. A nucleic acid encoding vitamin K-dependent polypeptide can be cloned into, for example, a baculoviral vector such as pBlueBac (Invitrogen, San Diego, Calif.) and then used to co-transfect insect cells such as *Spodoptera frugiperda* (Sf9) cells with wild-type DNA from *Autographa californica* multiply enveloped nuclear polyhedrosis virus (AcMNPV). Recombinant viruses producing the modified vitamin K-dependent polypeptides can be identified by standard methodology. Alternatively, a nucleic acid encoding a vitamin K-dependent polypeptide can be introduced into a SV40, retroviral, or vaccinia based viral vector and used to infect suitable host cells.

Mammalian cell lines that stably express vitamin K-dependent polypeptides can be produced by using expression vectors with the appropriate control elements and a selectable marker. For example, the eukaryotic expression vector pCDNA.3.1+ (Invitrogen, San Diego, Calif.) is suitable for expression of modified vitamin K-dependent polypeptides in, for example, COS cells, HEK293 cells, or baby hamster kidney cells. Following introduction of the expression vector by electroporation, DEAE dextran-, calcium phosphate-, liposome-mediated transfection, or other suitable method, stable cell lines can be selected. Alternatively, transiently transfected cell lines are used to produce vitamin K-dependent polypeptides. Vitamin K-dependent polypeptides also can be transcribed and translated in vitro using wheat germ extract or rabbit reticulocyte lysate.

Vitamin K-dependent polypeptides can be purified from conditioned cell medium by applying the medium to an immunoaffinity column. For example, an antibody having specific binding affinity for Factor VII can be used to purify modified Factor VII. Alternatively, concanavalin A (Con A) chromatography and anion-exchange chromatography (e.g., DEAE) can be used in conjunction with affinity chromatography to purify factor VII. Calcium dependent or independent monoclonal antibodies that have specific binding affinity for factor VII can be used in the purification of Factor VII.

Vitamin K-dependent polypeptides such as protein C can be purified by anion-exchange chromatography, followed by immunoaffinity chromatography using an antibody having specific binding affinity for protein C.

Vitamin K-dependent polypeptides also can be chemically synthesized using standard techniques. See, Muir, T. W. and Kent, S. B., Curr. Opin. Biotechnol., 1993, 4(4): 420–427, for a review of protein synthesis techniques.

Pharmaceutical Compositions

The invention also features pharmaceutical compositions including a pharmaceutically acceptable carrier and an isolated vitamin K-dependent polypeptide linked to a PEG polymer or an anticoagulant agent that includes at least two polypeptide monomers (described above). The pharmaceutical composition also can include an acute anticoagulant and an active-site inhibited factor VIIa polypeptide. The modified vitamin K-dependent polypeptide (e.g., PEG-linked and/or dimerized) is present in an amount effective to alter clot formation in a mammal. Useful vitamin K-dependent polypeptides of the pharmaceutical compositions can include, without limitation, PEG-linked APC, factor VIIai, factor IXai, factor Xai, or factor IIai, as discussed above. Pharmaceutical compositions also can include an additional anticoagulant agent such as aspirin, warfarin, or heparin.

The concentration of a modified vitamin K-dependent polypeptide effective to alter clot formation in a mammal may vary, depending on a number of factors, including the preferred dosage of the compound to be administered, the chemical characteristics of the compounds employed, the formulation of the compound excipients and the route of administration. The optimal dosage of a pharmaceutical composition to be administered may also depend on such variables as the overall health status of the particular patient and the relative biological efficacy of the compound selected. These pharmaceutical compositions may be used to regulate coagulation in vivo. For example, the compositions may be used generally for the treatment of thrombosis.

Vitamin K-dependent polypeptides that are linked to a PEG polymer or anticoagulant agents described above may be formulated into pharmaceutical compositions by admixture with pharmaceutically acceptable non-toxic excipients or carriers. Such compounds and compositions may be prepared for parenteral administration, particularly in the form of liquid solutions or suspensions in aqueous physiological buffer solutions; for oral administration, particularly in the form of tablets or capsules; or for intranasal administration, particularly in the form of powders, nasal drops, or aerosols. Compositions for other routes of administration may be prepared as desired using standard methods.

Formulations for parenteral administration may contain as common excipients sterile water or saline, polyalkylene glycols such as polyethylene glycol, oils of vegetable origin, hydrogenated naphthalenes, and the like. In particular, biocompatible, biodegradable lactide polymer, lactide/glycolide copolymer, or polyoxethylene-polyoxypropylene copolymers are examples of excipients for controlling the release of a compound of the invention in vivo. Other suitable parenteral delivery systems include ethylene-vinyl acetate copolymer particles, osmotic pumps, implantable infusion systems, and liposomes. Formulations for inhalation administration may contain excipients such as lactose, if desired. Inhalation formulations may be aqueous solutions containing, for example, polyoxyethylene-9-lauryl ether, glycocholate and deoxycholate, or they may be oily solutions for administration in the form of nasal drops. If desired, the compounds can be formulated as gels to be applied intranasally. Formulations for parenteral administration may also include glycocholate for buccal administration.

The invention will be further described in the following examples, which do not limit the scope of the invention described in the claims.

EXAMPLES

In all examples shown below, the proteins used are highly purified. Wild type VIIa or factor VIIa refer to a recombinant protein sold by NOVO Nordisk Company (Princeton, N.J.).

Example 1
Synthesis of PEG-linked, Active Site-directed Inhibitor of Factor VIIa and Other Proteases The chloromethylketone-derivatized peptides FFR and FPR (FFRck and FPRck, respectively, available from Calibochem or Bachem), were linked to PEG polymers. Commercially available PEG polymers were used that contained reactive groups able to derivatize free amino groups. One PEG polymer contained an activated ester based on a para-nitrophenol leaving group (polyoxyethylene bis para-nitrophenyl carbonate, PEG-NPC) and was obtained from Sigma Chemical Company (St. Louis, Mo., catalog number P9299). The average molecular weight of the PEG polymer was 3000±300. Other PEG polymers that were used contained a succinimidyl propionate (SPA) leaving group, one with a single chain of PEG having a molecular weight of 20,000 (catalog number 2M4M0P01 from Shearwater Polymers, Inc.), one having two chains of PEG, each with a molecular weight of 20,000 (product number 2Z3X0T01 from Shearwater Polymers, Inc.), and another having a molecular weight of 3400 (product number 4M4M0F02, Shearwater Polymers, Inc.).

Excess FFRck or FPRck (0.05 M) was mixed with PEG-3000 (0.02M) and allowed to react at room temperature at pH 8.5 for 14 hours. The product, PEG (3000)-FFRck, contained a PEG polymer covalently linked to the amino terminus of FFRck. The product was separated from unreacted peptide by gel filtration on Sephadex G-25. Reactions of $H_2N$-FPRck with PEG-20,000 and PEG(20,000)$_2$ were conducted in a similar manner but were complete within 2 hours at room temperature. Unreacted $H_2N$-FPRck was removed by dialysis of the reaction mixture against buffer for 48 hours. For both reactions, the amount of product formed was quantitated by UV absorbance of phenylalanine in the active site-directed inhibitor, using an extinction coefficient of 260 $M^{-1}$ $cm^{-1}$.

The PEG-3000 derivative (approximately 2:1 mol/mol of protein) was mixed with factor VIIa and allowed to react for 2 hr at room temperature in buffer (pH 7.5) containing 5 mM calcium. For quantitative reaction with the larger PEG derivatives, reactions were allowed to proceed for 15 hours at room temperature. Reaction with factor VIIa was monitored by loss of factor VIIa amidase activity toward the chromagenic substrate S-2288 (0.2 mM, Kabi) in a solution containing 100 nM soluble tissue factor (Dr. Walter Kisiel) and 5 mM calcium. When all factor VIIa activity was gone, the product was analyzed by standard SDS-PAGE methods.

Factor VIIa has a molecular weight of 50,000 and the expected molecular weight of the product was 53,000. On SDS-PAGE, however, PEG (3000)-VIIa migrated at a molecular weight greater than that of the bovine serum albumin standard (MW=67,000). SDS does not bind to the PEG portion of the molecule, which may account for the unusual migration in the gel. In addition, PEG is a very extended, unordered structure and may appear very large. The PEG (20,000)-VIIai migrated at an apparent molecular weight of 100,000, rather than at the expected molecular weight of 70,000. Again, the higher apparent molecular weight may stem from the PEG portion of the molecule.

When assayed by competition with factor VIIa (see below), the PEG-VIIai preparations had activity only slightly below that of the VIIai without PEG. Some reduction in activity was detected that correlated with the molecular weight of the PEG polymer. The PEG(3400)-Q10E32ai mutant had activity indistinguishable from the Q10E32ai protein. The PEG(20,000)-Q10E32ai and PEG(20,000)$_2$-Q10E32ai had activities approximately 40% that of the Q10E32ai molecule. This change may arise from a lower diffusion coefficient of the derivatized molecule. As the PEG polymer is very extended, it increases molecular volume much more than molecular weight. Diffusion coefficients, however, are proportional to molecular radius, while molecular volume is proportional to the particle radius cubed. Thus, a 2.5-fold decrease in diffusion can represent as much as a 6-fold increase in molecular volume. This decrease in function is small relative to the beneficial effect of PEG on circulation lifetime of these proteins.

Example 2
Synthesis of Bivalent Inhibitor from DTPA Anhydride

Active-site inhibitors were covalently linked to diethylenetriaminepentaacetic acid anhydride (DPTA), a bifunctional anhydride (Sigma Chemical Co., St. Louis, Mo.), to produce a bifunctional product. DPTA was slowly added as a solid to a solution of FFRck (0.04 M) at a pH 8.5 and reaction products were separated by HPLC. Samples were applied to a C18 column (Vydac) in reaction buffer. The column was washed with 0.1% triflunoacetic acid (TFA), and a gradient of 20–24% Acetonitrile in 0.1% TFA was applied from 4 to 24 minutes. A peak eluting at 20.8 minutes was identified by mass spectrometry as the desired bifunctional product DPTA-DiFFRck (molecular ion at 1358.2). A reaction product that eluted at 13.73 minutes was identified as the monovalent DTPA-FFRck product and had a monoisotopic mass of 876.

Example 3
Production of Vitamin K-dependent Polypeptide Homodimers

Factors VIIai-VIIai, VIIai(Q10E32)-VIIai(Q10E32) and Xai-Xai homodimers were generated using DPTA-DiFFRck. One equivalent of DPTA-DiFFRck was added to each of the protein solutions (0.15±0.05 mg/mL) and allowed to react at room temperature and a pH of 7.5 in the presence of 5 mM calcium. Formation of product was monitored by loss of amidase activity as described in Example 1. In some cases, phospholipid vesicles (1.5:1.0 w/w vesicles/protein) were added to increase the rate of product formation. Binding of proteases to the membrane is thought to place their active sites in close proximity and enhance production of the dimer. When all enzyme activity was inhibited, the product was isolated by gel filtration chromatography on a column of either Sephadex G-100 or Sephacryl S-200HR. The dimer eluted before monomeric protein and was identified by SDS-PAGE. The apparent molecular weights were appropriate for the dimeric proteins.

Dimeric, PEG modified factor VIIai containing the mutations P10Q/K32E was produced using a PEG-derivatized, bifunctional active-site inhibition reagent. A bifunctional SPA derivative of PEG (product number 4M4M0F02, Shearwater Polymers, Inc.) having a PEG molecular weight of 3400 (5.7 mg) was added slowly, as a solid, to a solution of FPRck (8.3 mg in 0.125 mL of 0.1 M HEPES buffer, pH 8.5). The reaction proceeded for 15 hr at room temperature and the product was separated from unreacted FPRck by chromatography on Sephadex G-25.

The PEG-derivatized, active-site inhibition reagent eluted at the exclusion volume of the G-25 column and was quantitated by absorbance of phenylalanine at 260 nm, as above. Equimolar quantities of PEG-derivatized active site inhibition reagent and mutant factor VIIa (44 pmol in 0.115 mL of 0.05 M Tris buffer pH 7.5 containing 0.1 M NaCl and 5 mM $CaCl_2$) were mixed and allowed to react at room temperature for 4 hours. After 1.5 hr, 4 $\mu$g of phospholipid vesicles (phosphatidylcholine/phosphatidylethanolamine/phosphatidylserine, 40/40/20) were added. Electrophoresis of the product showed approximately 30% yield of dimer with the rest of the protein migrating at the same position as PEG(3000)-VIIai. Analysis of activity of this mixed product by the competition assay described below showed that its inhibitor activity, on a weight basis, was equal to that of the monomeric VIIai mutant without PEG attached.

Example 4
Heterodimers of VIIai-Xai and Wild Type Vai-VIIai (Q10E32)

Factor VIIa was reacted with a 6-fold molar excess of bifunctional DPTA-DiFFRck reagent to prevent formation of a dimer of wild type VIIa. The product, VIIai-FFR-DPTA-FFRck, was separated from excess reagent by gel filtration on Sephadex G-25. The product then was reacted with factor Xa (bovine protein) to form VIIai-FFR-DPTA-FFR-Xa, also referred to as VIIai-Xai. Product was separated from monomeric proteins by gel filtration on Sephadex G-100. The molecular weight of the VIIai-Xai heterodimer was appropriate for this species (MWs of factor Xa and factor VIIa are 46,000 and 50,000, respectively).

Heterodimers of VIIai-VIIai(P10Q/K32E) were formed without isolation of intermediates. An equimolar quantity of DPTA-DiFFRck was mixed with a solution of factor VIIa (0.1 mg/mL) at room temperature and pH 7.5. Minimal amounts of dimeric VIIai, as estimated by SDS PAGE, were formed at these low protein concentrations. Equimolar amounts of mutant factor VIIa(P10QK32E) and phospholipid vesicles (1.5 g lipid/g protein) were added to the reaction mixture. Factor VIIa and VIIa(Q10E32) both can bind to the vesicles, facilitating formation of crosslinks. Analysis by SDS-PAGE indicated that the yield of dimer was over 50%. High yields of dimeric VIIai (>50%) only were obtained in reactions that contained phospholipid vesicles. Dimers were separated from monomeric proteins by gel filtration on Sephadex G-100. Heterodimers of mutant VIIa(P10Q/K32E) with factor Xa were formed with similar reaction conditions, adding Xa in the second step.

Homodimers of mutant factor VIIa(P10Q/K32E) were made directly by addition of bifunctional DTPA-DiFFRck to a mixture of protein and phospholipid vesicles. Since this mutant binds tightly to the membrane, it was easily dimerized by the bifunctional active-site inhibition reagent. Homodimers of factor Xa were made by the same methods.

Example 5
Superior Activity of Dimeric Enzymes

A competition assay was used to assess the affinity of various proteins for membrane-associated tissue factor. Both VIIa and active-site modified factor VIIa bind to tissue factor. Factor VIIai prevents VIIa from binding and prevents generation of active VIIa-tissue factor complex, resulting in a loss of VIIa-tissue factor activity, which can be monitored by coagulation time in factor VII-deficient human plasma. Briefly, varying amounts of the VIIai derivatives were mixed with tissue factor-membrane (1 $\mu$L of Innovin per 0.1125 mL of buffer-calcium solution containing 20 nM factor VIIa). Innovin (Dade Co.) is a commercial source of phospholipids and tissue factor. The reagents were allowed to equilibrate for 1 hr at 37° C. then factor VII-deficient human plasma (0.0375 mL) was added and the time needed to form a clot was measured by the manual hand tilt method.

Figure 2A:
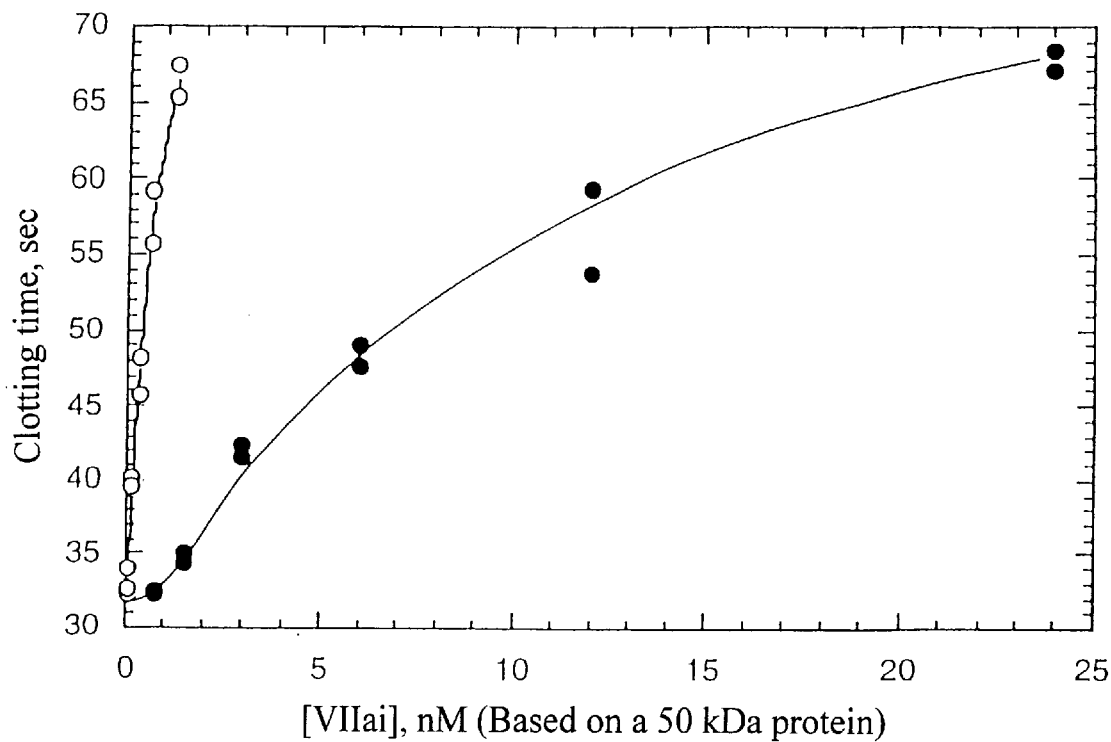
FIGS. 2A and 2B are graphs depicting activity of dimeric proteases.
Figure 3:
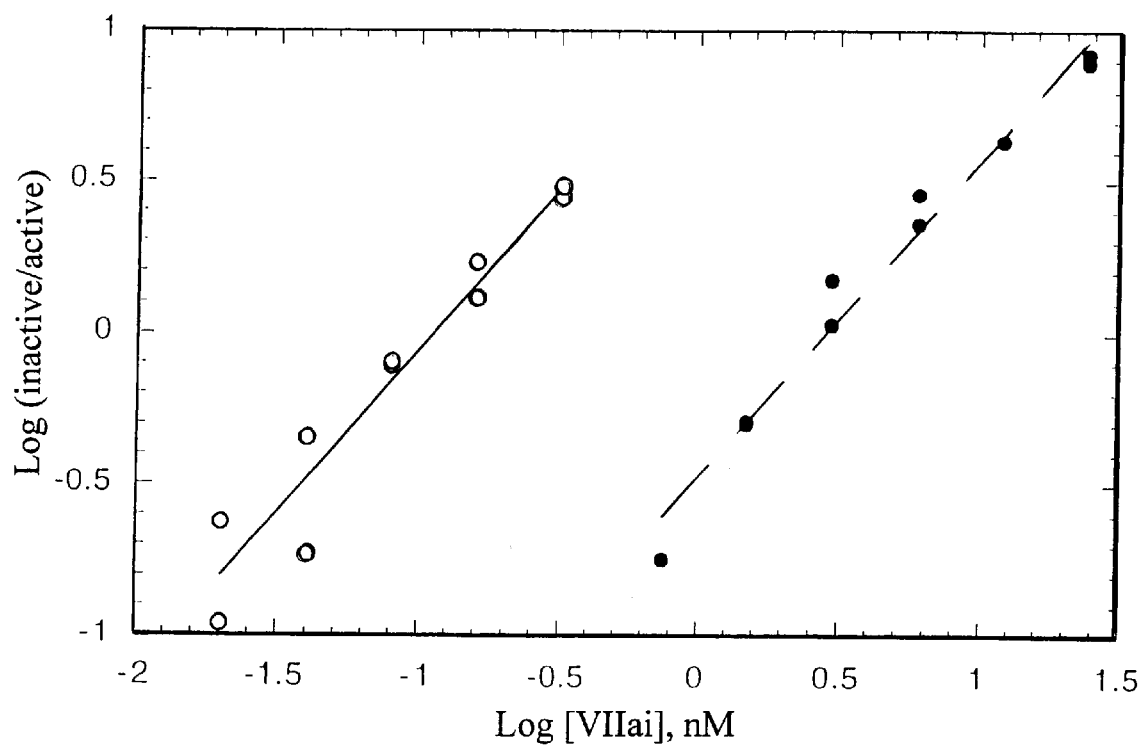
FIG. 3 is a Hill type plot of the activity of the VIIai (solid circles) vs. that of the heterodimer, VIIai-Xai (open circles).

FIG. 2A shows clotting time as a function of added VIIai-dimer and is compared with a similar titration with VIIai monomer. A large advantage of the dimeric protein is evident. To better compare these data, a Hill-type plot was created. Clotting times for various levels of VIIa-tissue factor, in the absence of VIIai, were determined and a standard curve created. The clotting times in FIG. 2A then were used in conjunction with the standard curve, to obtain the concentration of active VIIa-tissue factor complex in the solution. The level of inactive tissue factor-VIIai complex was then determined from equation 1:

Fraction of inactive complex=1−fraction of active complex      equation 1

Figure 2B:
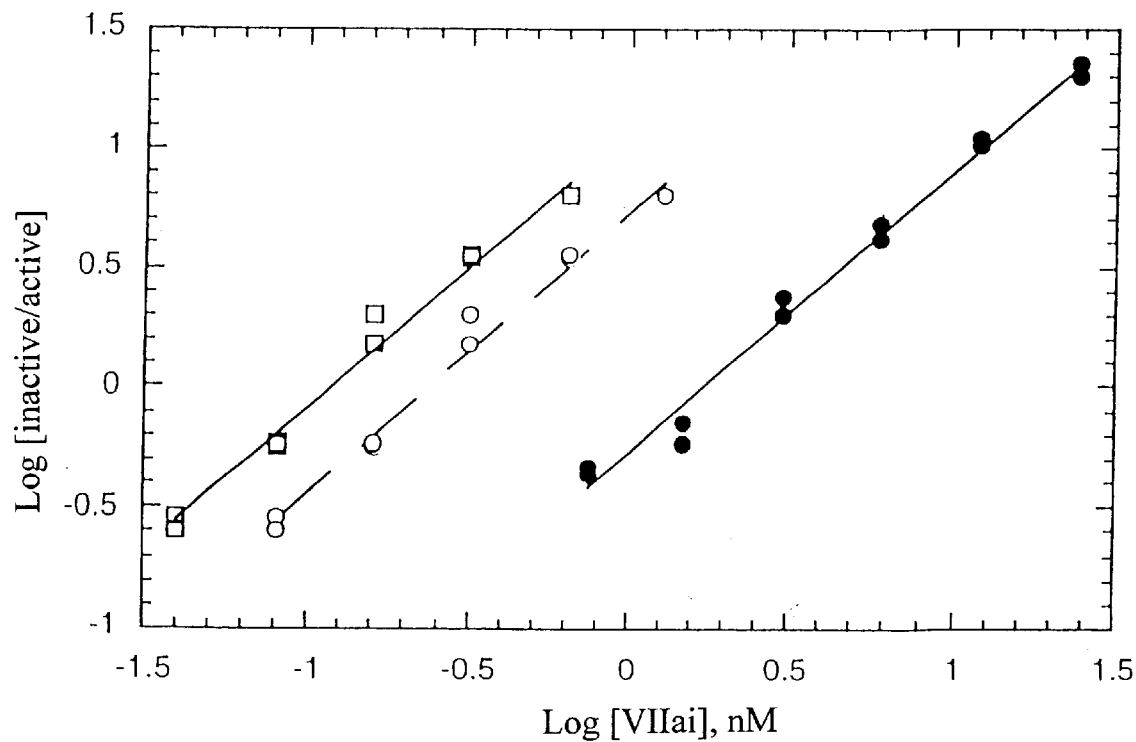

The results were plotted as log (inactive/active tissue factor) vs. log VIIai concentration in FIG. 2B. Two curves are shown for the dimeric protein. In one curve, the concentrations of all proteins were expressed on the basis of a 50kDa protein to compare the efficacy of dimer vs. monomer on a weight basis. The other curve used the molar concentration of dimer vs. the molar concentration of monomer. On a weight basis, dimeric VIIai had 16-fold higher activity than monomeric VIIai, while on a molar basis, the dimer was 32 times more active than the monomer.

Figure 4A:
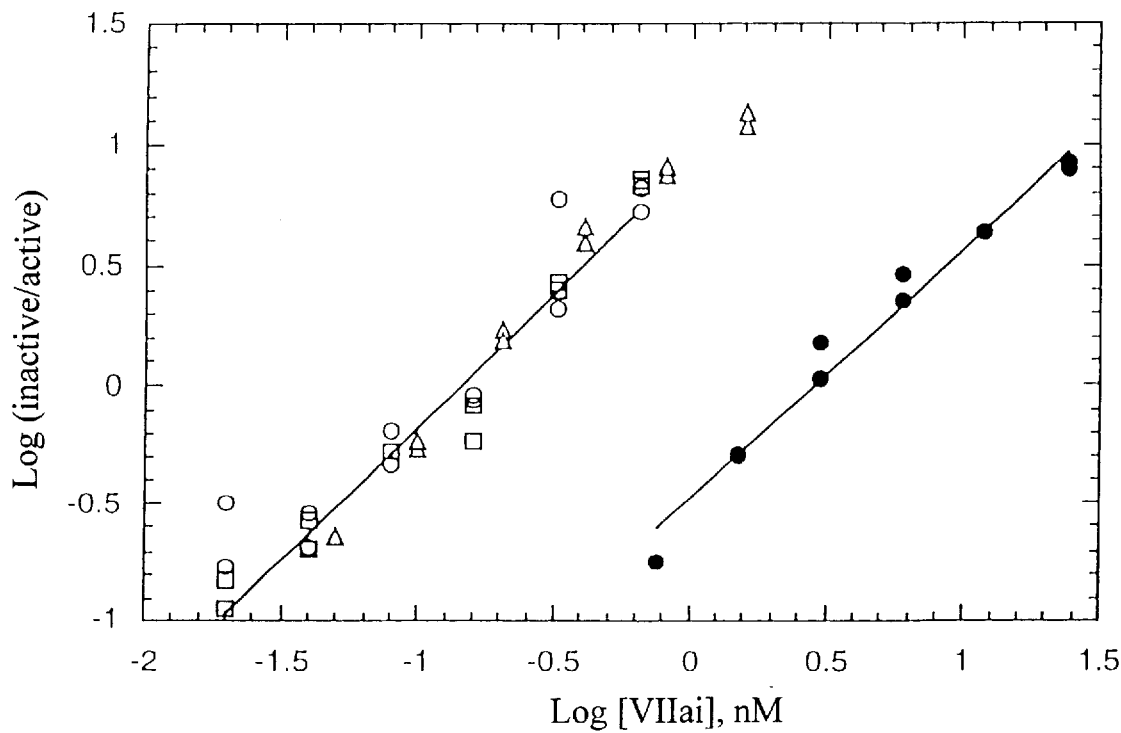
FIGS. 4A and 4B are Hill-type plots depicting activity of inactivated proteases.

The activity of the heterodimer, VIIai-Xai is shown in FIG. 3. This heterodimer had 13-times higher activity than the monomer when compared on a weight basis. Thus, on a weight basis, the homodimer of wild type VIIai and the heterodimer of VIIai-Xai had similar potency. The homodimer of VIIai(P10QK33E) had the same activity as its corresponding monomer (FIG. 4A). In the monomeric form, the Q10E32 mutant has much higher affinity than wild type factor VIIai due to an enhanced membrane binding site. Shah et al. (1998) *Proc. Natl. Acad. Sci. USA*, 95:4229–4234).

Figure 4B:
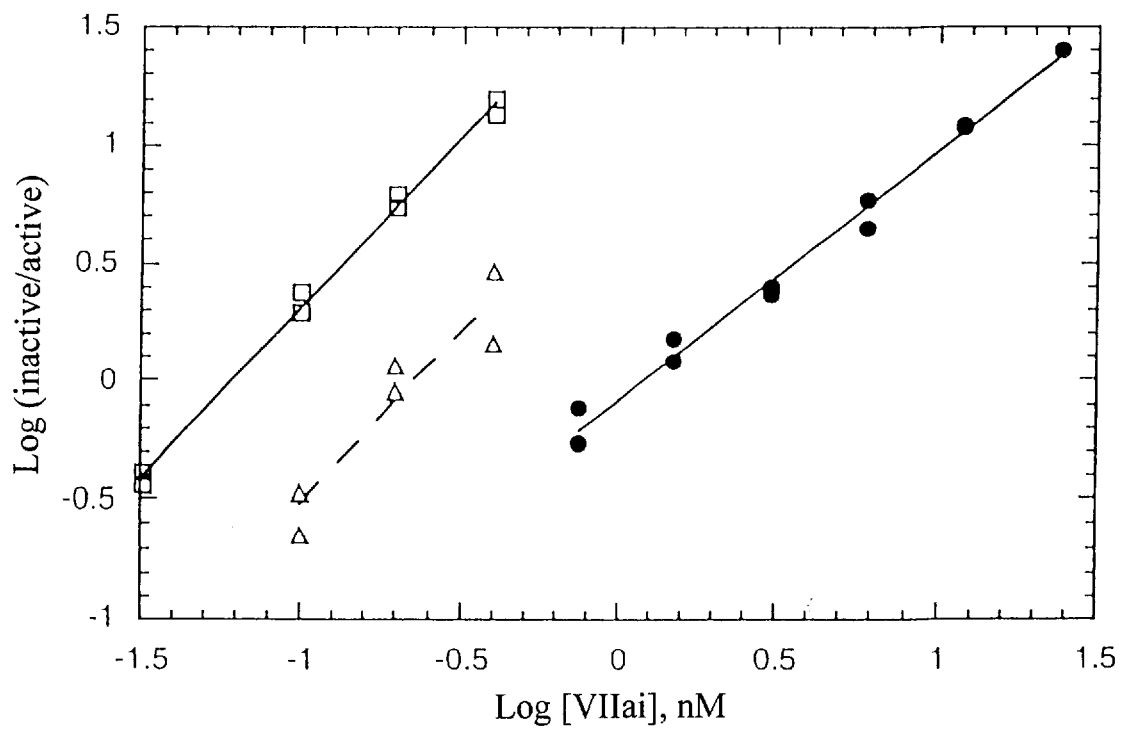
Figure 5:
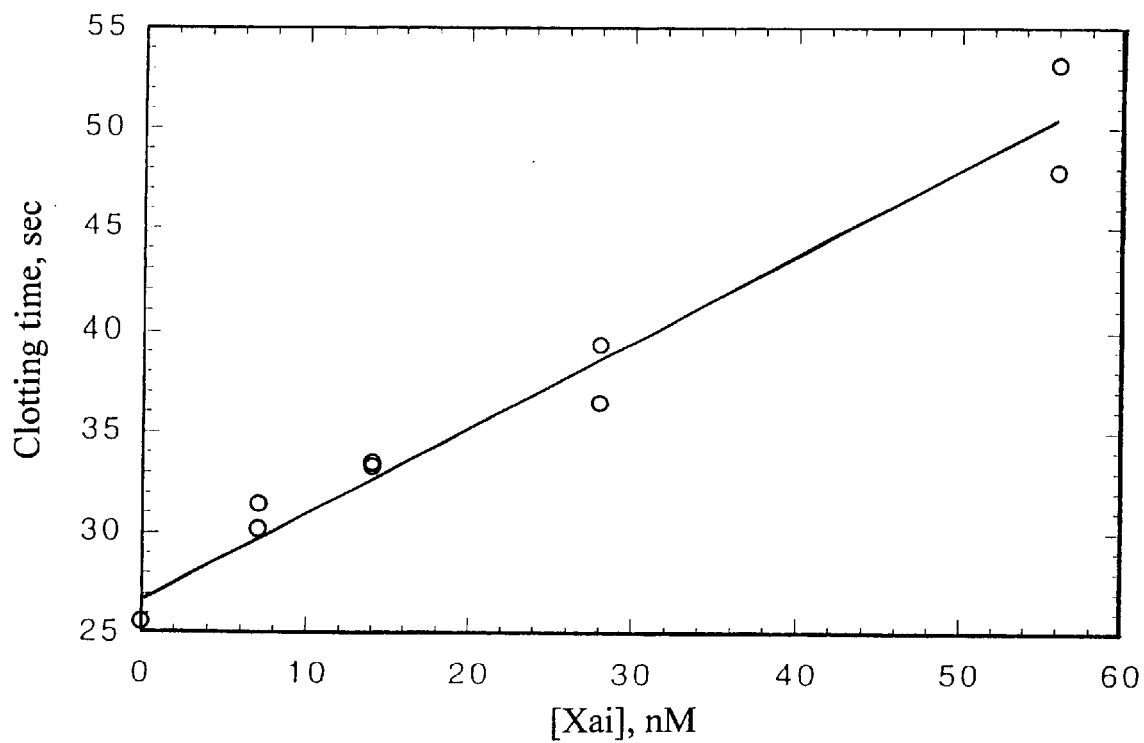
FIG. 5 is a graph of clotting time (in sec.) versus concentration of dimeric Xai (nM).

A heterodimer of mutant factor VIIai(P10Q/K32E) with wild type VIIai had the highest activity, 18-times that of monomeric wild type VIIai on a weight basis using titrations of the type and precision described above. This difference was on the basis of protein weight concentration. Surprisingly, the heterodimer of mutant VIIai(P10Q/K32E) with factor Xai had lower activity than the mutant monomeric protein (FIG. 4B). Thus, dimer formation can have different impacts depending on the proteins used. Again, use of a different crosslinking agent, with altered linker arm, may allow this heterodimer to express higher activity. A homodimer of factor Xa also was an effective inhibitor of blood coagulation (FIG. 5).

Example 6
PEG-modified Factor VIIa Retains Coagulation Activity

Factor VIIa (3.4 $\mu$M, 170 $\mu$g/mL) was derivatized with PEG-20,000-SPA at a 30:1 (reagent/protein) ratio in HEPES buffer, pH 8.5, and room temperature to produce factor VIIa with PEG randomly linked via lysine side chains. After reaction was complete (2 hours), the product was analyzed as described in Example 1. Amidolytic activity with soluble tissue factor was monitored and was 67% that of a control reaction. Coagulation activity was measured by a standard clotting assay in factor VII-deficient plasma. Calcium solution (37.5 $\mu$L of 20 mM) was the final component added to a mixture of 37.5 $\mu$l plasma, 1 $\mu$L of Innovin, and 75 $\mu$L of buffer. Clotting times were measured and compared to standards reactions with wild type factor VIIa. Coagulation activity of the derivatized protein was 55% that of the control. The reaction also was analyzed by SDS-PAGE, which indicated that almost all proteins had at least one PEG polymer attached. As expected from active site-directed derivatives, the mono-derivatized protein ran at an apparent molecular weight of 100,000. Other bands are detected at positions expected for two, three, and more PEG polymers per protein. This reaction showed that most of the enzyme activity survives one PEG polymer per enzyme.

High retention of activity was not obtained with activated protein C (APC), a protease that inhibits blood coagulation. That is, reaction with PEG and analysis of products by relevant blood clotting methods as well as SDS-PAGE showed that loss of APC activity approximately paralleled the formation of the mono-substituted protein. APC derivatized with a PEG-linked, active-site inhibitor may function as an inhibitor of prothrombinase.

Example 7
Analysis of Factor VIIa Function in Whole Blood of Hemophilia Patients Heparin anticoagulation typically is monitored with an ACT (activated clotting time) assay that measured clotting time of whole blood. Commercial instruments are available for this assay; experiments herein used the Hemochron Jr. Signature microcoagulation instrument from International Technidyne Corp. The ex vivo response of blood from five hemophilia patients to added VIIa was assessed. In order to conduct this analysis with low stress to hemophilia patients, blood from normal individuals also was examined by treatment with anti-factor VIII antibody to generate an ex vivo hemophilia A condition. Four normal individuals were tested in this manner. Representative results from both groups are shown in FIG. 6.

Blood was drawn and the coagulation time immediately determined in the ACT. A second portion of the blood was mixed with citrate (9 volumes of blood with 1 volume of 0.1M Na$_3$Citrate) to prevent coagulation. Clotting time was assayed according to manufacturer's instructions for analysis of blood. Normal procedure uses fresh, non-anticoagulated blood. For experimental purposes, blood was anticoagulated with sodium citrate and then recalcified just before use. Recalcification was achieved by mixing one equivalent of calcium (2.5 $\mu$L of 0.4 M CaCl$_2$ to 0.1 mL of anticoagulated blood) per equivalent of citrate used as the anticoagulant. This calcium was added just before loading the sample into the instrument. Blood that was anticoagulated and immediately recalcified gave clotting times that were 0–20% longer than the values obtained with the non-anticoagulated blood. This range was obtained for eight experiments performed on the four normal individuals. The range of clotting times for replicate measurements on each individual was about ±10%. Thus, anticoagulation and recalcification had a relatively small impact on clotting in the ACT. Most importantly, the clotting time for anticoagulated-recalcified blood was unchanged during storage at room temperature for 2 hr. The use of anticoagulated blood and its stability at room temperature allowed many samples to be run on one patient without the trauma of numerous blood withdrawals. Before each assay, the blood was mixed by gentle tipping of the plastic container.

Several types of cuvettes are supplied with the Hemochron Jr. instrument. The ACT+cuvette contains an agent to activate the contact phase of coagulation as well as additional phospholipid to support later steps of the coagulation cascade. This cuvette was not useful for factor VIIa assays; all four hemophilia patients gave clotting times (126–138 s) that were in the range of normal individuals. A second type of cuvette, the ACT-LR, contains material (Celite) to activate the contact phase of coagulation but has no added phospholipid. This assay depends on cellular membranes to support the later steps of coagulation. In both cuvettes, the range of clotting times for normal individuals tested in this study was 100–180 seconds. In severe hemophilia, activation of the contact phase of coagulation is without impact since factor VIII and/or IX are entirely absent. The presence of Celite or Kaolin is, however, beneficial for evaluation of hemophilia therapy as low levels of factor VIII and IX in some patients will contribute to coagulation. Thus, the ACT assay with the ACT-LR cuvette evaluates total coagulation potential from both the normal pathways and the high dose factor VIIa pathway.

Two hemophilia patients (I and II) had clotting times of >400 seconds in the ACT-LR cuvette. This is the upper limit of detection and the instrument simply shuts off. Normal individuals ranged from 126 seconds to 180 seconds. Two other hemophilia patients were described as moderately deficient. That is, they normally have >1% of the normal level of factor VIII or IX in their blood. One of these patients was factor VIII deficient (patient III) and the other patient was factor IX deficient patient IV). Their moderate deficiency was reflected in the ACT times of 350 and 290 s, respectively. Patient I was assayed on two occasions with the second occasion occurring 10 days after receiving an infusion of factor VIII. Although performed at such a distant time, the impact of this therapy was detected with the ACT, which gave a clotting time of 308 s rather than >400 s without therapy (above). Thus, the ACT was capable of detecting even modest therapy levels.

Figure 6A:
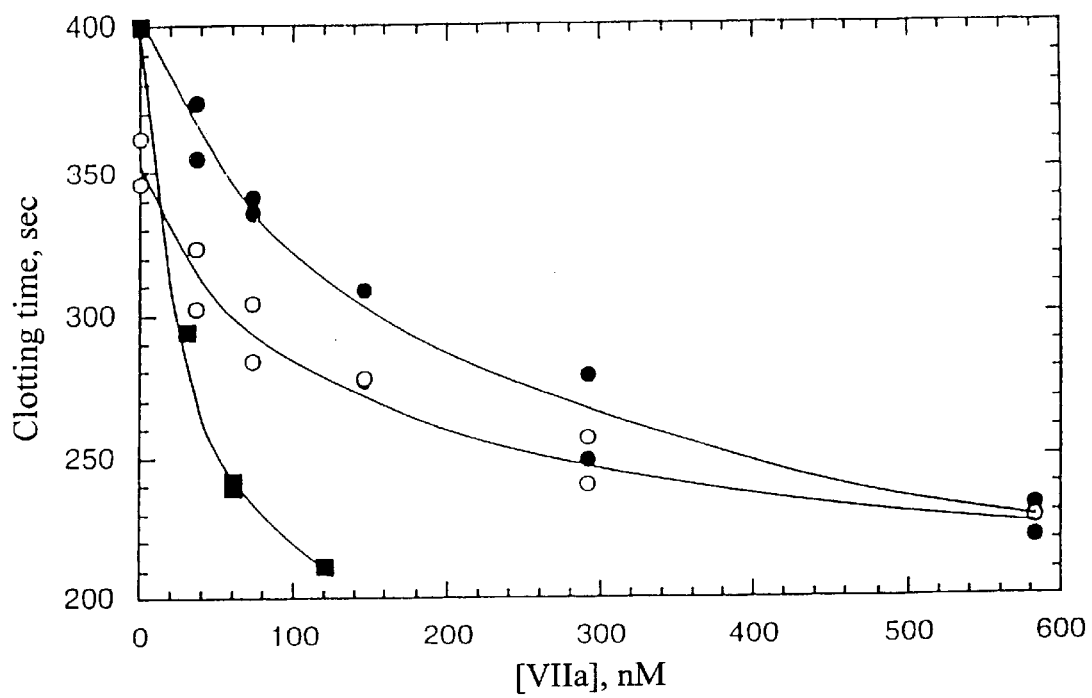
FIGS. 6A and 6B are graphs of clotting time (sec) versus factor VIIa concentration.

Titrations of hemophilia patients II and III with factor VIIa are shown in FIG. 6A. Factor VIIa lowered coagulation time of the blood, as expected for a therapeutic agent. The relative clotting potential can be estimated by comparing these times to target levels for normal individuals undergoing heparin anticoagulation therapy (for dialysis, 250–300 s, for angioplasty and other catheterization procedures, 300–350 seconds, and for bypass surgery, >400 seconds per the manufacturer of the Hemochron Jr.). The current therapy with VIIa results in a level of about 50 nM. FIG. 6A shows that this level of VIIa creates a coagulation potential similar to that of a normal patient who has been anti-coagulated for angioplasty (300–350s, FIG. 6A). This is a very modest coagulation potential. However, a modest potential is consistent with the need for repeated doses of VIIa administered over several hours (see above). Higher doses of VIIa resulted in decreased clotting time (FIG. 6). Extrapolation indicated that dosage levels of >1000 nM would be needed to approach normal clotting times (180s).

FIG. 6A shows that there was considerable patient variation with respect to response to VIIa. Patient III was about 2-fold more sensitive than patient II. Variability also was detected in the four normal individuals whose blood had been treated with anti-factor VIII antibodies. Those four individuals also showed a 2-fold variation in response to factor VIIa. Thus, the ACT analysis appears to provide an indication of individual patient responsiveness to VIIa, information that is valuable in setting individual dosages during therapy.

FIG. 6A also shows the responsiveness of patient II to the mutant factor VIIa containing the P10Q/K32E changes. This mutant has much higher affinity for the membrane and higher coagulation ability in tests such as those depicted in FIGS. 2 and 3. The greater potency of this mutant was readily detected in the ACT assay as well.

Titration of the second moderately severe hemophilia patient is not shown. However, factor VIIa had a much smaller impact. For example, the 290 second clotting time of patient IV was reduced to only 240 seconds at 300 nM VIIa, a change of only 50 seconds. The patient who had received factor VIII infusion 10 days prior to analysis showed no detectable impact of factor VIIa until over 200 nM. A plateau of clotting time appeared to be reached at 240 seconds.

Figure 6B:
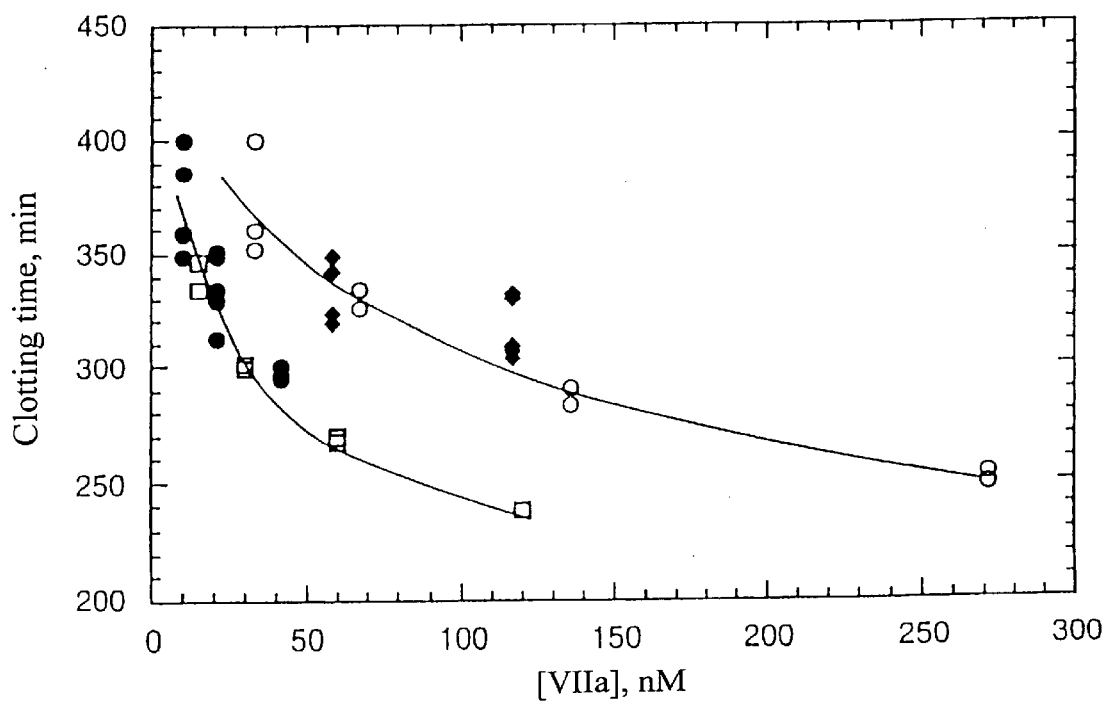

To create ex vivo hemophilia A (factor VIII deficiency), anticoagulated blood of four normal individuals was mixed with anti-factor VIII antibody (Enzyme Research Laboratories, Inc.). Sixty microliters of affinity purified antibody (protein absorbance at 280 nm=1.19) was mixed with 2 mL of blood. After 45 minutes at room temperature, the clotting time of all four individuals in the ACT-LR was greater than 400 minutes. Factor VIIa titrations for all artificial VIII-deficiency blood samples were carried out and an example is shown in FIG. 6B. All individuals showed a response to factor VIIa with clotting times reduced to easily detected levels. Responsiveness was similar to that of the hemophilia patients, with a 2-fold range of response by the four individuals, as discussed above. The range was to a higher VIIa requirement. That is, two individuals required twice the VIIa to achieve the response shown in FIG. 6B.

Response to VIIa was not predicted from other coagulation assays of the normal individuals, nor from their normal ACT clotting times. While all assays showed variation among the four normal individuals, shorter clotting time of two individuals in the classic APTT coagulation assay did not correlate with response to factor VIIa depicted in FIG. 6. The normal ACT times (without anti-VIII antibodies) also did not correlate with responsiveness to factor VIIa. Thus, assay with factor VIIa in the procedure shown in FIG. 6 may provide a unique measurement for monitoring and designing individual factor VIIa therapies.

As for the hemophilia patients, the ACT-LR showed a different response to wild type vs. mutant factor VIIa (VIIa-P10Q/K32E). The difference was 4-fold for the individual shown in FIG. 6B and ranged from 3.5 to 5-fold for the other three ex vivo factor VIII-deficient individuals. This was slightly less than the difference in the hemophilia patients. In any event, properties such as individual variation, protein specificity, detection of moderate vs. severe deficiency, and detection of therapy conducted after extended times suggest that the test shown in FIG. 6 monitors important features of factor VIIa therapy in hemophilia.

Factor VIIa that had been modified by random reaction of PEG with lysines residues (see Example 6) also was tested. The molar concentration of active, modified VIIa was calculated from the amidolytic activity of the preparation versus that of a known concentration of unmodified factor VIIa. On this basis, activity of the PEG-modified protein was very similar to that of unmodified factor VIIa. The range of individual points for the PEG proteins (see FIG. 6B) was greater than that that observed for normal VIIa. Greater variation for PEG proteins when assayed in the Hemochron Jr. signature microcoagulation analyzer was also detected during factor VIIa titration of blood from a hemophilia patient with factor VII deficiency.

Overall, limited PEG modification of factor VIIa by random derivatization of lysine residues can be used to generate an effective factor VIIa population.

Example 8

Circulation Lifetime of Proteins in the Mouse

The mouse is an excellent experimental animal for study of factor VIIai turnover in the circulation. Murine tissue factor does not recognize human factor VII with high affinity and protein turnover can be studied without severe anticoagulation of the mouse.

Factor VIIai was injected into the tail vein of the mouse at time zero then blood (20 $\mu$L) was obtained from a small tail injury at various later times. The blood was anticoagulated with 0.1 M $Na_3$Citrate (9 parts blood to 1 of anticoagulant) and plasma was obtained after centrifugation of the cells. Factor VIIai then was assayed using equilibrium conditions, i.e., a competitive assay where VIIa and VIIai were allowed to reach equilibrium with available tissue factor before coagulation was started. The following procedure was developed to allow this condition without interference from coagulation proteins in the mouse plasma. The mouse plasma was diluted 1:49 in 0.05 M Tris buffer, pH 7.5 (containing 0.1 M NaCl and BSA, 1 mg/mL), and Innovin (9 $\mu$L/mL) and calcium (to 6.7 mM) were added to activate the clotting proteins in the diluted mouse plasma. After 2 hr, the blood clotting proteases were inhibited by addition of diisopropylfluorophosphate (DIFP) to a concentration of 2 mM. After 12 hours at room temperature, the excess DIFP had spontaneously hydrolyzed and the solutions were assayed for inhibitor proteins. Fractions (0.28 to 5 $\mu$L) of the diluted, activated and inhibited plasmas were added to 112.5 $\mu$L of buffer containing Innovin (1 $\mu$L) and 30 pM factor VIIa in calcium- and BSA-containing buffer. After equilibration at 37° C. for 1 hr, factor VII-deficient plasma (37.5 $\mu$L) was added and clotting time recorded. The amount of inhibitor in the plasma was determined from this clotting time and by comparison to clotting times of reactions containing no inhibitor plasma but known amounts of factor VIIai. Initial levels of VIIai in the mouse plasma were 0.33–0.65 $\mu$M, representing 50–75% of the theoretical level. The theoretical level was calculated from the assumptions that injection of the protein was quantitative and that a 20 g animal has 1.0 mL of plasma. A small level of inhibitor was detected in control mouse plasma (0.01±0.005 nM) and this was subtracted as a background.

Figure 7A:
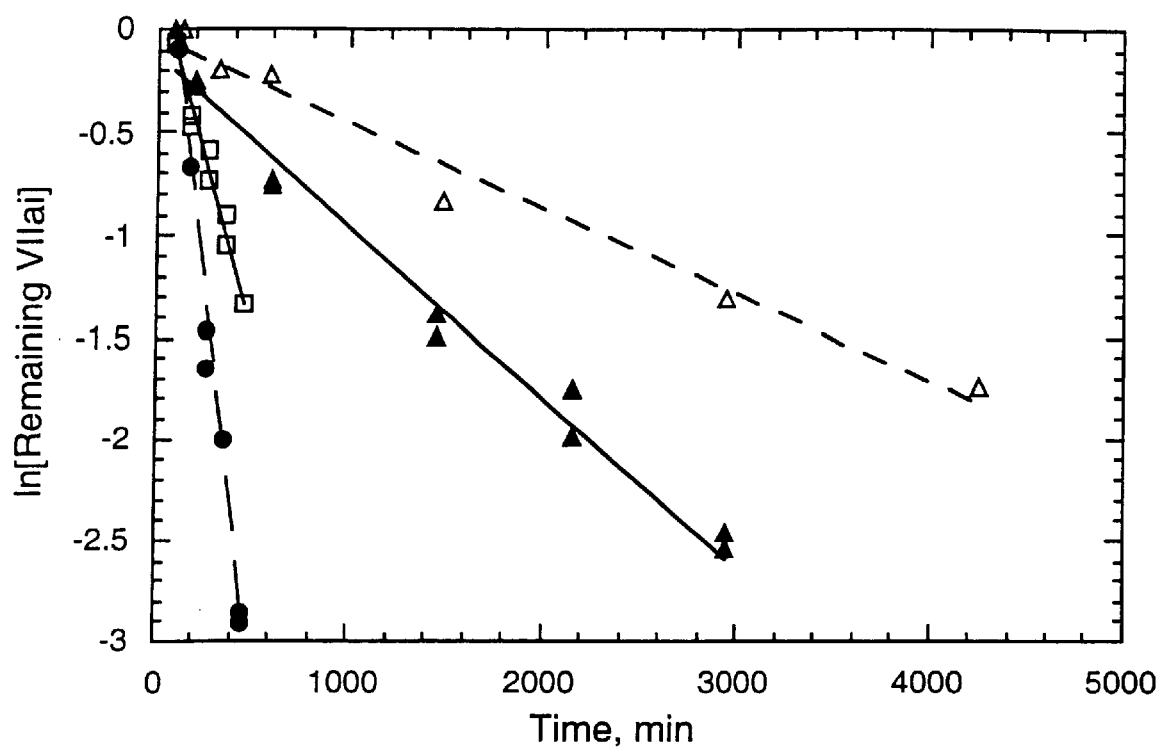
FIGS. 7A and 7B are graphs depicting the circulation time for various factor VIIai proteins in the mouse.

First order decay plots for disappearance of several different factor VIIai molecules from the plasma are shown in FIG. 7A. For direct comparison, all levels of inhibitor are expressed as a fraction of the inhibitor present at the first time point, 80 minutes. Linear analysis of the data provides an estimate of the rate constant for disappearance of VIIai. For wild type VIIai, the average and SD for 3 animals was −0.0074±0.0002/min. This corresponds to a circulation half-life of 94 minutes. PEG(3000)-VIIai was removed from the circulation of two animals with rate constants of −0.0033/min and −0.0034/min, corresponding to a circulation half-time of 207 minutes (2.2-times longer than that of the standard VIIai).

Active site-modified PEG(20,000)-VIIai was removed from the circulation of three experimental animals with a rate constant 0.00081/min±0.00003, corresponding to a circulation half-life of 14 hours. This represents a 10-fold enhancement over normal VIIai. Finally, PEG(20,000)$_2$-VIIai was removed from the circulation of two animals with rate constants of −0.00041/min (data shown) and −0.00044/min (data not shown), corresponding to an average circulation half-time of 27 hours. This is nearly 20-fold longer than that of the monomeric protein. Given that larger species such as the human tend to have much longer protein circulation lifetimes than the mouse, it appears likely that truly extended therapy in the human might be achieved with PEG-derivatized proteins.

Figure 7B:
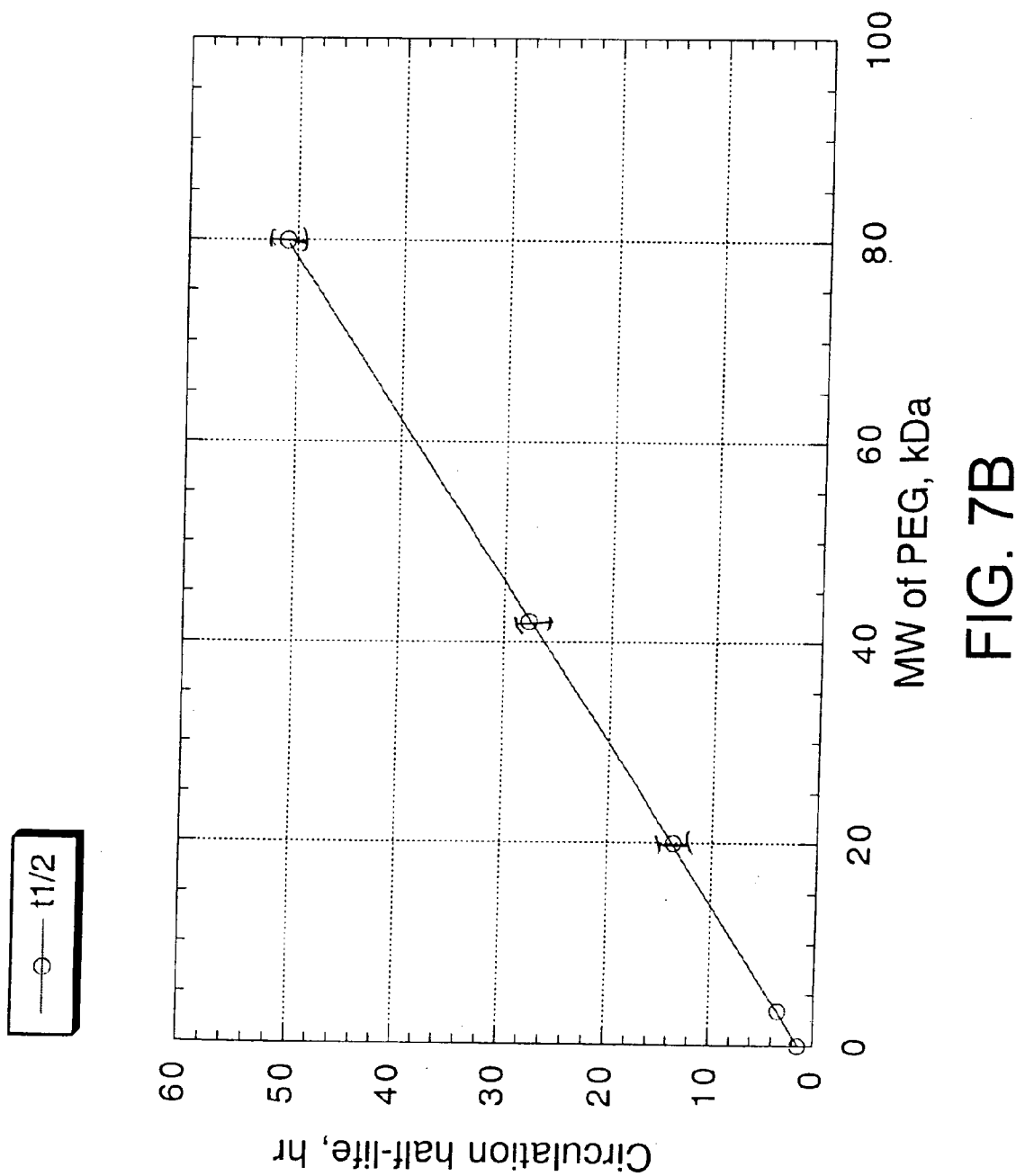

FIG. 7B shows the relationship between molecular weight of the PEG polymer and circulation half-time. The linear relationship was surprising and did not correlate with reports for Fv fragment of immunoglobulins, where an upper limit to circulation time was reported. Thus, it appears that even longer circulation lifetimes are possible for the vitamin K-dependent proteins, provided that larger PEG polymers are attached.

Figure 8A:
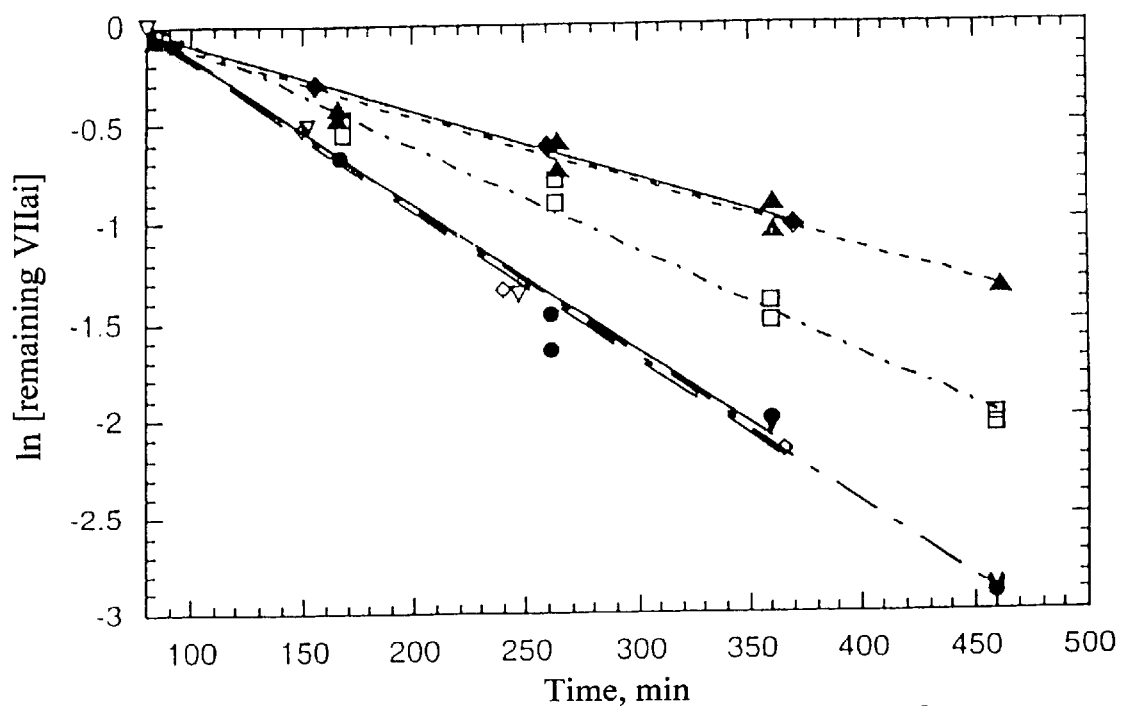
FIGS. 8A and 8B are graphs depicting the circulation time for factor VIIai proteins.

Circulation of other materials is shown in FIG. 8. All three animals given the VIIai proteins are shown in FIG. 8A, along with PEG(3000)-VIIai and dimeric VIIai. The dimer gave a rate constant for disappearance from the blood stream of −0.0052/min, corresponding to a circulation half-time of 139 minutes. Similar results were obtained with the factor VIIai-Xai heterodimer. Thus, a 3000 molecular weight PEG polymer was more effective than protein dimerization with respect to impact on circulation time. The impact of PEG cannot be explained by simple molecular weight change, since dimeric factor VIIai has a molecular weight of 100,000 while PEG(3000)-VIIai has a molecular weight of 53,000.

Figure 8B:
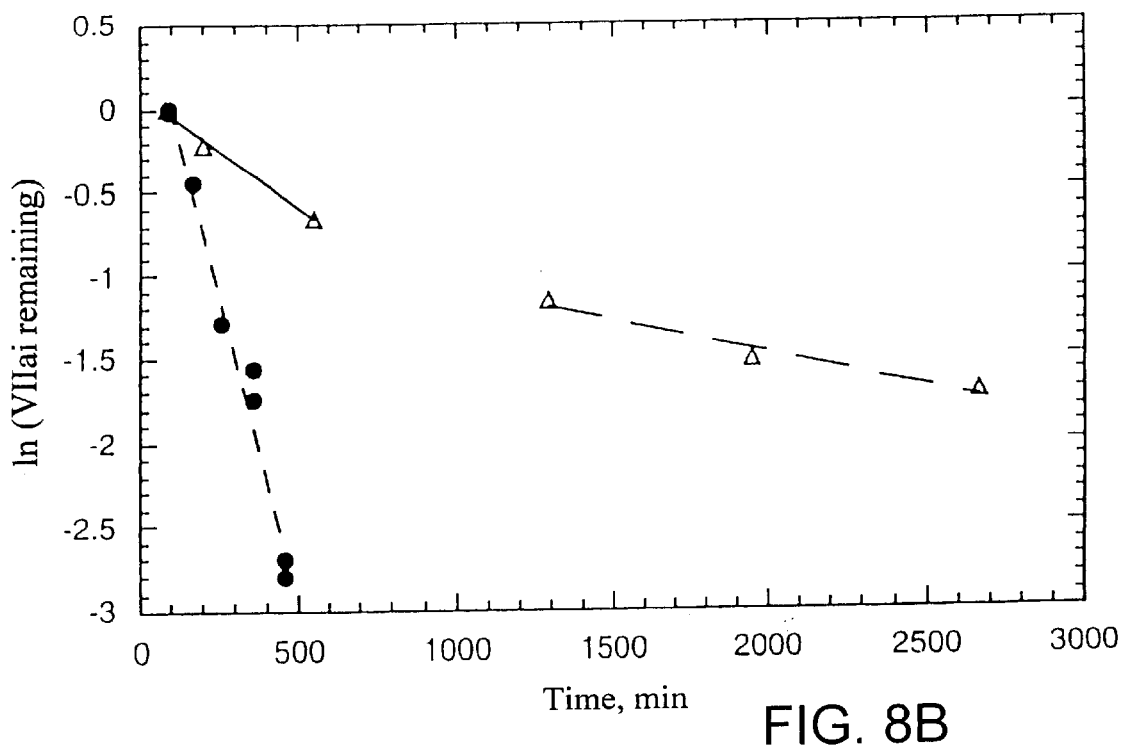

Turnover of VIIai containing random PEG modification of surface lysines is shown in FIG. 8B. Although the VIIa-PEG polymer mixture of Example 6 had activity that was a third less than that of the standard VIIai in the competitive assay described in FIG. 2, the loss of potency was more than offset by increases in circulation time of the derivative. Disappearance from the circulation was biphasic. The initial 50% of the inhibitor activity was lost with a rate constant of −0.00138/min, corresponding to a circulation half-time of 9 hours. This may represent a combination of molecules with no PEG (circulation halftime of 94 min) and mono-derivatized factor VIIai (circulation half-time of 14 hr). The second half of the activity was lost with a rate constant of −0.0004/min. This corresponded to a circulation half-time of 29 hours, very similar to the rate of disappearance of active site modified PEG(20,000)$_2$-VIIai (FIG. 7A). It is possible that this half-time is for protein molecules with two PEG polymers. This suggests that the result in FIG. 7B can be extended to addition of PEG to these proteins, by any mechanism. Thus, increases in circulation half-times appear to be based on molecular size or weight of the PEG polymer.

To test for the impact of PEG(20,000)-CO-FPRck administration, animals were injected four times (0.25 ml volume) with a total of 50 nmols of reagent into one animal over an 8 hr time period. Clotting assays did not detect an increase in coagulation inhibitors in this animal (assayed by the method outlined in example 8, above), indicating that little inhibition of blood coagulation proteases had occurred in those animals. If proteases were inhibited, prolonged circulation lifetime would cause them to accumulate and an increase of blood coagulation inhibitors would be observed. Over a period of 12 hours, there was no increase in the level of clotting inhibitors in this animal. Thus, PEG reagent containing the active site-directed group may not pose a toxicity problem to an animal. It is possible that excess PEG-modified active site reagent may not need to be removed from a reaction mixture before administration to an animal.

Example 9

Acute Versus Chronic Anticoagulation

Figure 9A:
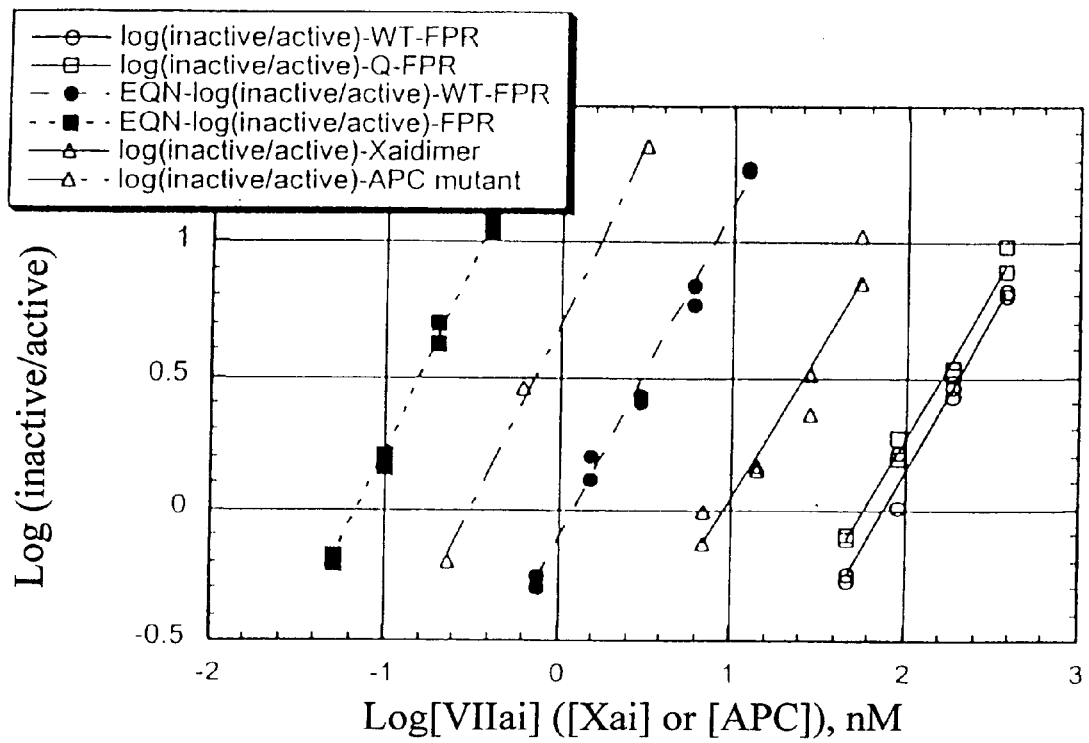
FIGS. 9A and 9B are graphs comparing acute versus chronic anticoagulation.

FIG. 9A shows anti coagulation by VIIai in an 'acute' situation. In this example, factors VIIa and VIIai are both present and calcium is added to initiate the coagulation reaction, mimicking the sudden exposure of tissue factor to the blood stream during injury. As indicated in FIG. 9A, factor VIIai requires very high concentrations to inhibit the acute state. To compare the results of acute and chronic situations, factor VIIai concentrations in the acute reaction have been adjusted to recognize the concentrations VIIa (100 pM) in the acute experiment vs. that in the equilibrium experiment (5.6 nM). For comparison, results for factor Xai (data from FIG. 5) and activated protein C (wild type and a H10Q/S11G/Q32E/N33D mutant, data from Nelsestuen et al. (1999) Trends. Cardiovasc. Med., 9:162–167) also are shown in FIG. 9. Of these anticoagulants, factor VIIai is the least effective for acute state anticoagulation. APC is effective for treating acute anticoagulation, although it is rapidly inhibited in the blood and has a very short lifetime. Interestingly, the high affinity mutants are not very much better than wild type protein. Lack of difference can be explained by a reaction limited by diffusion of particles in solution. Association rate constants estimated for VIIa binding to tissue factor are $2 \times 10^9$ $M^{-1}s^{-1}$, very near to the collisional rate constant. If acute anticoagulation is dependent on collisional rates, higher affinity will not have an impact. Only at equilibrium, when dissociation rates are also part of the interaction, will the high affinity mutants become effective.

Also shown in FIG. 9A is the inhibition by factor VIIai under equilibrium or chronic conditions. At equilibrium, the higher efficacy and therefore the benefit of VIIai and its mutant P10Q/K32E become apparent. At equilibrium, 30 nM VIIai is sufficient to block a high level of coagulation (>90% inhibition). However, in acute anticoagulation, 30 nM VIIai is quite ineffective. It appears that VIIai is most desirable in anticoagulation of chronic situations while other inhibitors are more desirable for inhibition of acute situations.

Figure 9B:
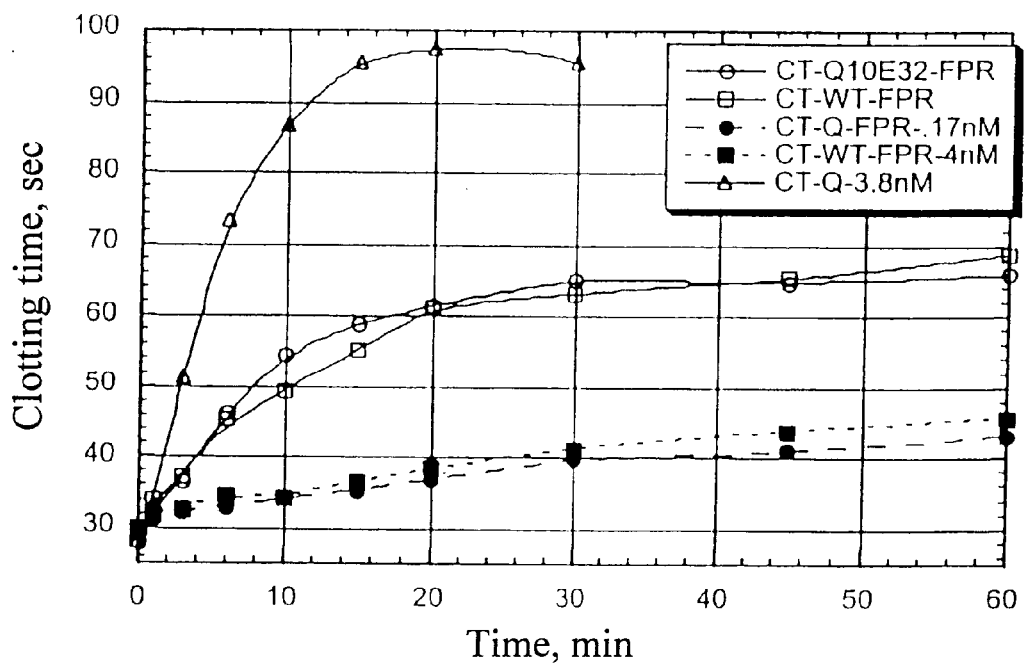

The time course for conversion from acute to chronic inhibition is illustrated by the results in FIG. 9B. Low levels of VIIai, insufficient to inhibit acute coagulation but creating high inhibition at equilibrium, were used. The time course for conversion to the inhibited state was determined by coagulation at various times after mixing. It is apparent that conversion to equilibrium conditions required 10 to 20 minutes. Thus, chronic inhibition by VIIai fits any situation where tissue factor may be exposed for this time or longer.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated vitamin K-dependent polypeptide linked to a polyethylene glycol (PEG) polymer, wherein said vitamin K-dependent polypeptide is a protease selected from the group consisting of factor VIIa, factor IXa, factor Xa, factor IIa, and activated protein C, and wherein said protease is further linked to an active-site inhibition reagent.

2. The polypeptide of claim 1, wherein said active-site inhibition reagent is a chloromethylketone derivatized amino acid or peptide.

3. The polypeptide of claim 1, wherein said PEG polymer is linked to said protease via said active-site inhibition reagent.

4. The polypeptide of claim 1, wherein said protease is factor VIIa.

5. The polypeptide of claim 1, wherein said protease is factor IXa.

6. The polypeptide of claim 1, wherein said protease is factor Xa.

7. The polypeptide of claim 1, wherein said protease is activated protein C.

8. The polypeptide of claim 1, wherein said protease is factor IIa.

9. A pharmaceutical composition comprising an isolated vitamin K-dependent polypeptide linked to a PEG polymer, wherein said vitamin K-dependent polypeptide is a protease selected from the group consisting of factor VIIa, factor IXa, factor Xa, factor IIa, and activated protein C, and wherein said protease is further linked to an active-site inhibition reagent.

10. The pharmaceutical composition of claim 9, wherein said active-site inhibition reagent is a chloromethylketone derivatized amino acid or peptide.

11. The pharmaceutical composition of claim 9, wherein said PEG polymer is linked to said protease via said active-site inhibition reagent.

12. The pharmaceutical composition of claim 9, wherein said protease is factor VIIa.

13. The pharmaceutical composition of claim 9, wherein said protease is factor IXa.

14. The pharmaceutical composition of claim 9, wherein said protease is factor Xa.

15. The composition of claim 9, wherein said protease is activated protein C.

16. The composition of claim 9, wherein said protease is factor IIa.

* * * * *

UNITED STATES PATENT AND TRADEMARK OFFICE
CERTIFICATE OF CORRECTION

| | | |
|---|---|---|
| PATENT NO. | : 6,423,826 B1 | |
| APPLICATION NO. | : 09/607716 | |
| DATED | : July 23, 2002 | |
| INVENTOR(S) | : Gary L. Nelsestuen | |

It is certified that error appears in the above-identified patent and that said Letters Patent is hereby corrected as shown below:

Page 1, Column 1, lines 7-9, please delete "Funding for work described herein was provided in part by the federal government, which may have certain rights in the invention." and insert --Funding for work described herein was provided in part by the National Institutes of Health, grant no. HL60859. The federal government may have certain rights in the invention.-- therefor.

Signed and Sealed this

Twenty-sixth Day of June, 2007

JON W. DUDAS
*Director of the United States Patent and Trademark Office*